(12) United States Patent
Diwu et al.

(10) Patent No.: US 11,237,170 B2
(45) Date of Patent: Feb. 1, 2022

(54) STYRYL PHENOLS, DERIVATIVES AND THEIR USE IN METHODS OF ANALYTE DETECTION

(71) Applicant: AAT BIOQUEST, INC., Sunnyvale, CA (US)

(72) Inventors: Zhenjun Diwu, Sunnyvale, CA (US); Zhen Luo, San Carlos, CA (US); Jixiang Liu, Santa Clara, CA (US); Pengfei Dong, San Jose, CA (US)

(73) Assignee: AAT BIOQUEST, INC., Sunnyvale, CA (US)

( * ) Notice: Subject to any disclaimer, the term of this patent is extended or adjusted under 35 U.S.C. 154(b) by 134 days.

(21) Appl. No.: 16/350,574

(22) Filed: Dec. 4, 2018

(65) Prior Publication Data
US 2020/0174006 A1 Jun. 4, 2020

(51) Int. Cl.
*G01N 33/58* (2006.01)
*C07D 333/04* (2006.01)
*G01N 33/532* (2006.01)

(52) U.S. Cl.
CPC ........... *G01N 33/58* (2013.01); *C07D 333/04* (2013.01); *G01N 33/532* (2013.01); *G01N 2223/406* (2013.01); *G01N 2800/7028* (2013.01)

(58) Field of Classification Search
CPC ................. G01N 33/532; G01N 33/58; G01N 2223/406; G01N 2800/7028; C07D 333/04
See application file for complete search history.

(56) References Cited

U.S. PATENT DOCUMENTS

| | | |
|---|---|---|
| 4,521,511 A | 6/1985 | Stout |
| 4,598,044 A | 7/1986 | Kricka et al. |
| 4,745,181 A | 5/1988 | Law et al. |
| 4,835,101 A | 5/1989 | Kao et al. |
| 4,842,997 A | 6/1989 | Carter et al. |
| 4,857,455 A | 8/1989 | Khanna et al. |
| 4,918,192 A | 4/1990 | Law et al. |
| 4,946,958 A | 8/1990 | Campbell et al. |
| 5,006,461 A | 4/1991 | Woiszwillo |
| 5,043,269 A | 8/1991 | Theodoropulos |
| 5,079,150 A | 1/1992 | Wagner et al. |
| 5,110,932 A | 5/1992 | Law et al. |
| 5,196,306 A | 3/1993 | Bobrow et al. |
| 5,215,890 A | 6/1993 | Theodoropulos et al. |
| 5,238,817 A | 8/1993 | Bobrow et al. |
| 5,418,138 A | 5/1995 | Miller et al. |
| 5,565,570 A | 10/1996 | Mattingly et al. |
| 5,583,001 A | 12/1996 | Bobrow et al. |
| 5,656,426 A | 8/1997 | Law et al. |
| 5,731,158 A | 3/1998 | Bobrow et al. |
| 5,783,699 A | 7/1998 | Mattingly et al. |
| 6,280,962 B1 | 8/2001 | Cohen |
| 6,335,173 B1 | 1/2002 | Kaplan |
| 6,355,443 B1* | 3/2002 | Bobrow ............... C07D 213/30 435/28 |
| 6,828,109 B2* | 12/2004 | Kaplan ............ G01N 33/56972 435/30 |
| 6,852,503 B1 | 2/2005 | Clothier |
| 6,897,036 B2 | 5/2005 | Akhavan-Tafti et al. |
| 7,563,566 B2 | 7/2009 | Woerner et al. |
| 8,192,948 B1 | 6/2012 | Feather-Henigan |
| 8,778,624 B2 | 7/2014 | Natrajan et al. |
| 9,091,691 B2 | 7/2015 | Lohse |
| 9,377,465 B2 | 6/2016 | Lohse et al. |
| 9,575,062 B2 | 2/2017 | Natrajan et al. |
| 9,671,400 B2 | 6/2017 | Lohse |
| 9,958,449 B2 | 5/2018 | Lohse et al. |
| 9,970,874 B2 | 5/2018 | Lohse et al. |

FOREIGN PATENT DOCUMENTS

DE 10255894 A1 * 6/2004 ............... C12Q 1/28
EP 2634576 A1 9/2013

OTHER PUBLICATIONS

Karkmann et al., "Enzymatic signal amplification for sensitive detection of intracellular antigens . . . ," J. Immunol. Meth. (1999) vol. 230, pp. 113-120.

Chao, et al., "Immunofluorescence Signal Amplification by the Enzyme-Catalyzed . . . ," Cytometry (1996) vol. 23, pp. 48-53.

Malisius, et al., "Constant Detection of CD2, CD3, CD4 and CD5 in Fixed and Paraffin-enbedded . . . " J Histochem Cytochem (1997) vol. 45, pp. 1665-1672.

* cited by examiner

Primary Examiner — Shafiqul Haq
(74) Attorney, Agent, or Firm — Fenwick & West LLP

(57) ABSTRACT

Styryl compounds useful for preparing biological detections probes, and the use of the Styryl compounds for the detection, discrimination and quantification of biological targets.

16 Claims, 5 Drawing Sheets

STYRYL PHENOLS, DERIVATIVES AND THEIR USE IN METHODS OF ANALYTE DETECTION

FIELD OF THE INVENTION

The present invention relates to styryl phenol compounds and compositions which react with a peroxidase and/or a peroxide to generate a color, fluorescence or luminescence that can be viewed by naked eyes and/or detected by an optical device in the absence or presence of another enzyme. In particular, the present invention relates to improved compositions containing styryl phenol compounds which react with a peroxidase and a peroxide to produce an enhanced and optically detectable signal. The invention further relates to assay methods for detecting a peroxidase and for detecting peroxidase-labeled specific binding partners in immunoassays, nucleic acid probe assays and other specific binding pair assays.

BACKGROUND OF THE INVENTION

Detection of a target biological marker in a biological sample, a specimen, or on a surface, may be achieved by contacting the target with a molecule which specifically binds to the target. The molecule may be, for example, a protein or a nucleic acid probe for use in in situ hybridization or Southern or northern blots. The molecule may be linked, either directly or indirectly to a detectable substance, thus permitting the staining and detection of the target contained in a biological sample.

Detectable agents that are commonly used include biotin, DIG, DNP, proteins, dyes such as Texas red, and FITC, as well as radioactive isotopes, metal particles and enzymes which upon catalysis of a specific substrate permit colormetric detection of the target biological marker. One system for the detection of biological markers relies on immunologically derived molecules which specifically bind to a desired target or a biological marker in a sample.

Immunologically-based detection of biological markers advantageously exploits the specificity of immune-derived proteins such as antibodies for specific biological markers of interest. Typically, the antibody will recognize a specific epitope on the biological target marker which permits the target to be distinguished and thus detected from other biological markers contained within a given biological sample or specimen. A variety of formats capable of detecting biological markers of interest are known, including enzyme linked immuno-assays (ELISA), flow cytometry, western blots, radioimmunoassay (RIA) and immunohistochemistry (IHC). All of these techniques are useful in research as well as in the detection and diagnosis of a variety of diseases and conditions.

IHC specifically provides a method of detecting a biological marker in a sample or tissue specimen in situ. The overall cellular integrity of the sample is maintained in IHC, thus allowing detection of both the presence and location of the biological marker of interest. Typically, a sample is fixed and cut into sections for viewing by light microscopy. The intensity of the signal obtained correlates with the level of expression of the target molecule in the sample. Early methods for performing IHC relied solely on direct detection. Direct detection means the detectable agent, e.g., a fluorescent dye, is linked directly to the primary antibody, which is the antibody that specifically binds to the target biological marker. The limitation of this method is that biological markers expressed at low levels produce a weak detection signal. Attempts to overcome this limitation include linking multiple copies of the primary antibody to a dextran polymer conjugated with an enzyme such as horse radish peroxidase (HRP).

Other attempts to overcome this problem include addition of a second antibody. To amplify the detection, the primary antibody is not labeled. Instead, a secondary antibody, linked to a detectable substance that specifically binds to the primary antibody, is added to the method. Multiple copies of the secondary antibody can bind the primary antibody, thus enhancing the signal. This method is known as indirect detection.

Among all the sensitive detection tags, peroxidase enzymes (such as HRP) are most frequently used as markers or labels in enzyme-linked assays for biological molecules and other analytes of interest such as drugs, hormones, steroids and cancer markers. Optical detection of these enzymes offers a safe, convenient and sensitive means of measuring the amount of enzyme in a sample or the amount of an enzyme-labeled analyte or labeled specific binding partner for an analyte. Many substrates have been developed to quantify the level of particular peroxidase enzymes, including aniline derivatives such as OPD, DAB, TMB, AEC and luminol (U.S. Pat. Nos. 5,006,461; 5,079,150; 5,238,817; 5,418,138; 6,897,036; 7,563,566), phenol derivatives such as ADHP, ferulic amides, tyramides and homovanillic acid (U.S. Pat. Nos. 4,521,511; 4,598,044, 4,835, 101, 4,842,997; 4,857,455; 6,280,962; 6,335,173; 6,852, 503; 6,828,109; 8,192,948; 9,377,465), acridinium esters (U.S. Pat. Nos. 4,745,181; 4,918,192; 4,946,958; 5,110,932; 5,565,570; 5,656,426; 5,783,699; 8,778,624; 9,575,062) and other compounds such as ABTS and indolines, etc. (E.P. Pat No. 2,634,576; U.S. Pat. Nos. 5,043,269; 5,215,890).

Various methods have been described for assaying biological samples with amplified reporter systems using the above-mentioned peroxidase substrates. Among them, tyramide-derived substrates are considered to be one of the most sensitive detection methods for assaying peroxidase-based biological systems (U.S. Pat. Nos. 6,280,962; 6,335, 173; 6,852,503; 6,828,109; 9,091,691; 9,671,400; 9,958, 449; 9,970,874). Bobrow et al. describe methods for detecting or quantitating analytes using an analyte dependent enzyme activation system as well as catalyzed reporter deposition (CARD) methods. Specifically, Bobrow et al. describes colorimetric and fluorometric solid phase enzyme immunoassays which are enhanced by amplification of the reporter molecules (U.S. Pat. Nos. 5,196,306; 5,583,001; 5,731,158). Chao et al. describes a CARD system that uses horseradish peroxidase substrate Cy3.29-tyramide to deposit fluorogen molecules onto fixed tissues and cells as well as proteins bound to nitrocellulose membranes, with up to a 15-fold increase over standard indirect immunofluorescence methods (Cytometry 1996, 23, 48-53). Malisius et al. describe a method for enhancing detection of leukocyte antigens in formalin-fixed tissue samples (J Histochem Cytochem, 1997, 45, 1665-1672). However, tyramide compounds still have a few drawbacks. Tyramide Signal Amplification (TSA) is not superior to conventional techniques for detecting surface antigens on live cells due to the high level of spontaneous activation and non-specific binding of the fluorescent substrate to live cell membranes (U.S. Pat. No. 6,335,173). Karkmann et al. report that the direct detection of fluorochrome-labeled tyramide is problematic probably due to hydrophobic interactions with the cell membranes (J. Immunol. Meth. 1999, 230, 113-120).

DEFINITIONS

Figure 1:
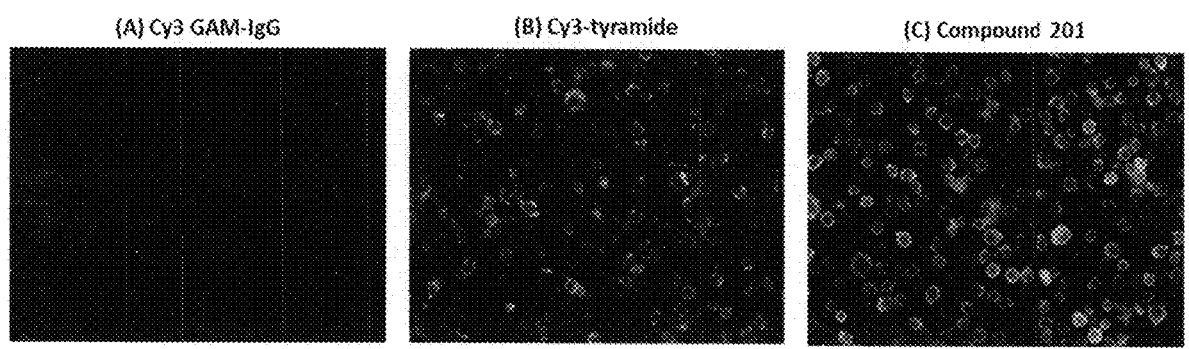
FIG. 1. Fluorescence images of CD45 detection in Jurkat-T cells. Cells are fixed and stained for CD 45 by a standard method using Goat anti-Mouse IgG secondary antibody directly conjugated with Cy3 (A), or by amplified methods using HRP-labeled Goat anti-Mouse IgG secondary antibody followed by Cy3-tyramide (B) or Compound 201 (C), respectively. These images indicate that the Compound 201-amplified method is more sensitive than both the tyramide amplified method and Cy3 direct labeling method.
Figure 2:
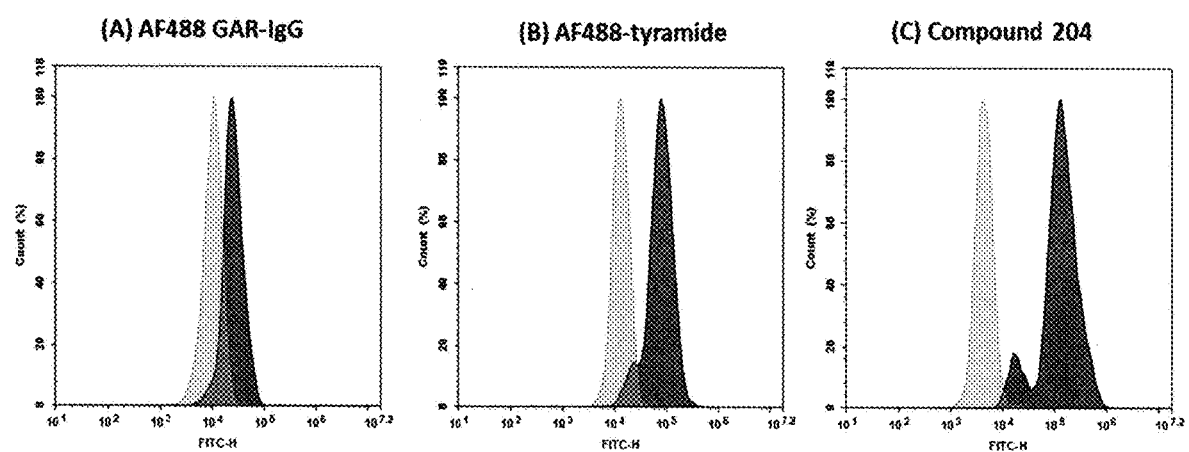
FIG. 2. Flow cytometric analysis of pAKT expression (Akt 1 phospho, pS473) in Jurkat-T cells. Cells are fixed, permeabilized, and stained for pAKT (black histograms) using a Goat anti-Rabbit IgG secondary antibody directly conjugated with Alexa Fluor 488 (A), or by amplified methods using HRP-labeled Goat anti-Rabbit IgG secondary antibody followed by AF488-tyramide (B) or Compound 204 (C) respectively. The control cells are incubated without pAKT but stained under the same conditions (gray histograms). The PSA amplified method provides a 30-fold increase in signal/background ratio compared to the directly labeled secondary antibodies. In addition, the Compound 204-amplified method shows much higher sensitivity than the corresponding AF488-tyramide amplified method.
Figure 3:
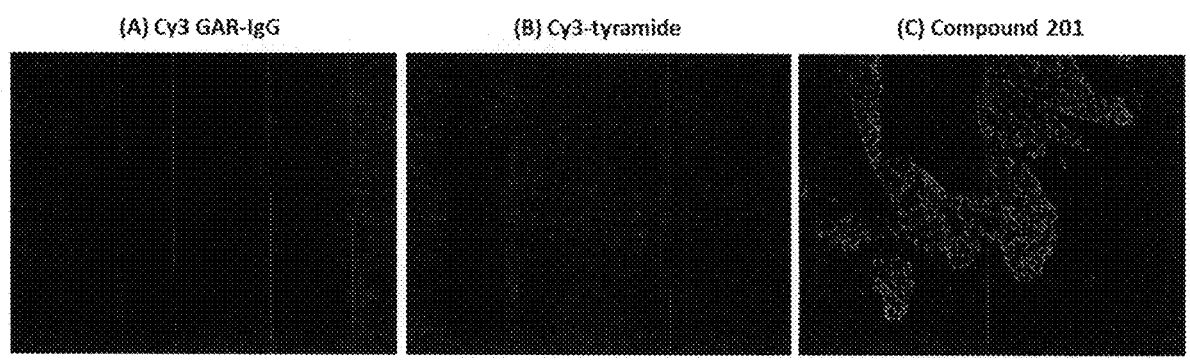
FIG. 3. Fluorescence images of EpCAM in FFPE tissue sections. Human lung adenocarcinoma sections are stained for EpCAM using a Goat anti-Rabbit IgG secondary antibody directly conjugated with Cy3 (A) or using amplified methods with a polyHRP-conjugated Goat anti-Rabbit IgG secondary antibody followed by Cy3-tyramide (B) or Compound 201 (C), respectively. Compound 201 demonstrates much higher sensitivity than the Cy 3 direct labeling and Cy 3 tyramide-amplified method.
Figure 4:
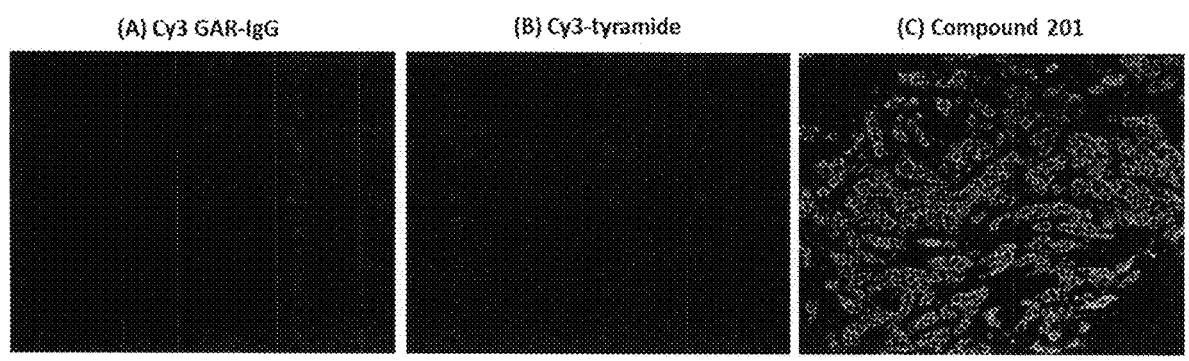
FIG. 4. The Human Her2/Neu (c-erbB-2) positive tissue sections are stained for HER2/ErbB2 using a Goat anti-Rabbit IgG secondary antibody directly conjugated with Cy3 (A), or by amplified methods using a polyHRP-conjugated Goat anti-Rabbit IgG secondary antibody followed with Cy3-TSA (B) or Compound 201 (C), respectively. Images show that Compound 201-amplified method can significantly increase the sensitivity of fluorescence IHC signal compared to the Cy3-directly labeled method and Cy3-tyramide-amplified method.
Figure 5:
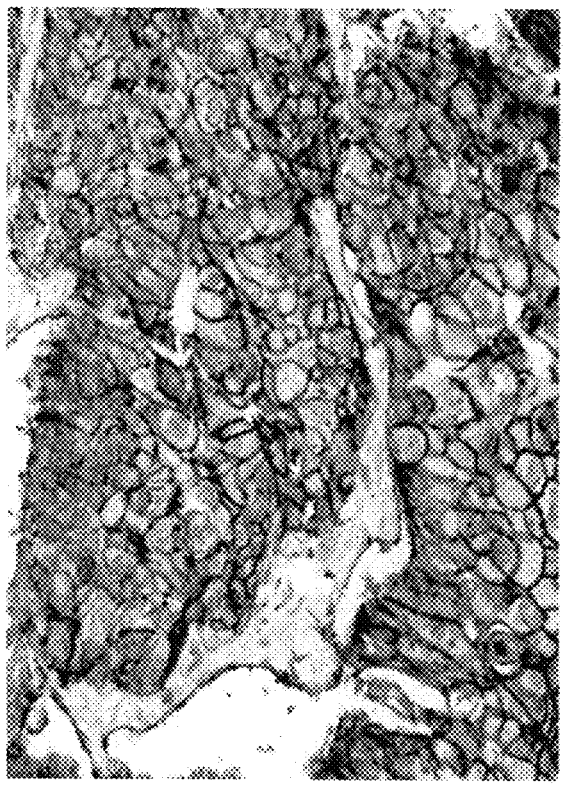
FIG. 5. IHC staining of EpCAM detection in FFPE lung adenocarcinoma tissues (See Example 28). The tissue sections are incubated with polyHRP GAR-IgG conjugate and then stained with DAB (left) or with Compound 201 (right), respectively.
Figure 5:

The following definitions are set forth to illustrate and define the meaning and scope of the various terms used to describe the invention herein.

The term "organic substituent", as used herein, refers to a carbon-containing organic radical that incorporates straight, branched chain or cyclic radicals having up to 50 carbons, unless the chain length or ring size is limited thereto. The organic substituent may include one or more elements of unsaturation, such as carbon-carbon double or triple bonds. Organic substituents may include alkyl, alkylene, alkenyl, alkenylene and alkynyl moieties, among others.

The term "alkyl," as used herein, by itself or as part of another group, refers to straight, branched chain or cyclic radicals having up to 50 carbons and 10 heteroatoms, unless the chain length or ring size is limited thereto, such as methyl, ethyl, propyl, cyclopropanyl, isopropyl, butyl, t-butyl, isobutyl, pentyl, hexyl, cyclohexyl, isohexyl, heptyl, 4,4-dimethylpentyl, octyl, 2,2,4-trimethylpentyl, nonyl, and decyl, among others. The alkyl moieties may be substituted or contain other moieties including but not limited to carbonyl, ester, urea, urethane, sulfonamide, sulfone, sultone, or amide groups.

The term "alkylene" as employed herein, by itself or as part of another group, refers to straight, branched chain or cyclic divalent radicals having up to 50 carbons, unless the chain length or ring size is limited thereto. Typical examples include methylene (—CH$_2$—), ethylene (—CH$_2$CH$_2$—), propylene, butylene, pentylene, hexylene, heptylene, octylene, nonylene, and decylene, among others.

The term "alkenyl," as used herein, by itself or as part of another group, means a straight, branched chain or cyclic radical having 2-50 carbon atoms and one or more carbon-carbon double bonds, unless the chain length or ring size is limited thereto, such as ethenyl, 1-propenyl, 2-propenyl, 2-methyl-1-propenyl, 1-butenyl, and 2-butenyl, among others. The alkenyl chain may be 2 to 10 carbon atoms in length. Alternatively, the alkenyl chain may be 2 to 4 carbon atoms in length.

The term "alkenylene," as used herein, by itself or as part of another group, means straight, branched chain or cyclic divalent radical having 2-50 carbon atoms, unless the chain length or ring size is limited thereto, said straight, branched chain or cyclic radical containing at least one carbon-carbon double bond. Typical examples include ethenylene (—CH=CH—), propenylene (—CH=CHCH$_2$— and —CH$_2$CH=CH—), n-butenylene, and 3-methyl-2-pentenylene, hexenylene, heptenylene, octenylene, nonenylene, and decenylene, among others.

The term "alkynyl," as used herein, by itself or as part of another group, means a straight, branched chain or cyclic radical of 2-50 carbon atoms, unless the chain length or ring size is limited thereto, having at least one carbon-carbon triple bond between two of the carbon atoms in the chain, such as acetylenyl, 1-propynyl, and 2-propynyl, among others. The alkynyl chain may be 2 to 10 carbon atoms in length. Alternatively, the alkynyl chain may be from 2 to 4 carbon atoms in length.

The term "alkynylenc" as used herein, by itself or as part of another group, means a straight, branched chain or cyclic divalent radical having 2-50 carbon atoms, unless the chain length or ring size is limited thereto, that contains at least one carbon-carbon triple bond. Typical examples include ethynylene (—C≡C—), propynylene (—C≡CCH$_2$— and —CH$_2$C≡C—), n-butynylene, 4-methyl-2-pentynylene, 1-butynylene, 2-butynylene, 3-butynylene, 4-butynylene, pentynylene, hexynylene, heptynylene, octynylene, nonynylene, and decynylene, among others.

The term "alkoxy" as used herein, by itself or as part of another group, refers to any of the above radicals linked via an oxygen atom. Typical examples include methoxy, ethoxy, isopropyloxy, sec-butyloxy, n-butyloxy, t-butyloxy, n-pentyloxy, 2-methylbutyloxy, 3-methylbutyloxy, n-hexyloxy, and 2-ethylbutyloxy, among others. Alkoxy also may include PEG groups (—OCH$_2$CH$_2$O—) or alkyl moieties that contain more than one oxygen atom. The alkoxy moieties may be substituted or contain other moieties including but not limited to carbonyl, ester or amide groups.

The term "aryl," as employed herein, by itself or as part of another group, refers to an aryl or aromatic ring system containing 1 to 4 unsaturated rings (each ring containing 6 conjugated carbon atoms and no heteroatoms) that are optionally fused to each other or bonded to each other by carbon-carbon single bonds, that is optionally further substituted as described below. Examples of aryl ring systems include, but are not limited to, substituted or unsubstituted derivatives of phenyl, biphenyl, o-, m-, or p-terphenyl, 1-naphthyl, 2-naphthyl, 1-, 2-, or 9-anthryl, 1-, 2-, 3-, 4-, or 9-phenanthrenyl and 1-, 2- or 4-pyrenyl. Aryl substituents may include phenyl, substituted phenyl, naphthyl or substituted naphthyl. The aryl moieties may be substituted or contain other moieties including but not limited to carbonyl, ester, urea, urethane, sulfonamide, sulfone, sultone, or amide groups.

The term "heteroaryl," as employed herein, by itself or as part of another group, refers to groups having 5 to 14 ring atoms; 6, 10 or 14 t electrons shared in a cyclic array; and containing carbon atoms and 1, 2, 3, or 4 oxygen, nitrogen or sulfur heteroatoms (where examples of heteroaryl groups are: thienyl, benzo[b]thienyl, naphtho[2,3-b]thienyl, thianthrenyl, furyl, pyranyl, isobenzofuranyl, benzoxazolyl, chromenyl, xanthenyl, phenoxathiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, carbazolyl, phenanthridinyl, acridinyl, perimidinyl, phenanthrolinyl, phenazinyl, isothiazolyl, phenothiazinyl, isoxazolyl, furazanyl, phenoxazinyl, and tetrazolyl groups). The heteroaryl moieties may be substituted or contain other moieties including but not limited to carbonyl, ester, urea, urethane, sulfonamide, sulfone, sultone, or amide groups.

Any aryl or heteroaryl ring system is unsubstituted or optionally and independently substituted by any synthetically accessible and chemically stable combination of substituents, such as H, halogen, cyano, sulfo, alkali or ammonium salt of sulfo, nitro, carboxy, alkyl, perfluoroalkyl, alkoxy, alkylthio, amino, monoalkylamino, dialkylamino or alkylamido, the alkyl portions of which having 18 or fewer carbons.

The terms "halogen" or "halo" as employed herein, by itself or as part of another group, refers to chlorine, bromine, fluorine or iodine.

The terms "amino" or "amine" include $NH_2$, "monoalkylamine" or "monoalkylamino," and "dialkylamine" or "dialkylamino". The terms "monoalkylamine" and "monoalkylamino," "dialkylamine" and "dialkylamino as employed herein, by itself or as part of another group, refers to the group $NH_2$ where one hydrogen has been replaced by an alkyl group, as defined above.

The terms "dialkylamine" and "dialkylamino" as employed herein, by itself or as part of another group, refers to the group $NH_2$ where both hydrogens have been replaced by alkyl groups, as defined above.

The term "hydroxyalkyl," as employed herein, by itself or as part of another group, refers to an alkyl group where one or more hydrogens thereof are substituted by one or more hydroxyl moieties.

The term "haloalkyl," as employed herein, by itself or as part of another group, refers to an alkyl group where one or more hydrogens thereof are substituted by one or more halo moieties. Typical examples include chloromethyl, fluoromethyl, difluoromethyl, trifluoromethyl, trichloroethyl, trifluoroethyl, fluoropropyl, and bromobutyl, among others.

The term "haloalkenyl," as employed herein, by itself or as part of another group, refers to an alkenyl group where one or more hydrogens thereof are substituted by one or more halo moieties.

The term "haloalkynyl," as employed herein, by itself or as part of another group, refers to an alkynyl group where one or more hydrogens thereof are substituted by one or more halo moieties.

The term "carboxyalkyl," as employed herein, by itself or as part of another group, refers to an alkyl group where one or more hydrogens thereof are substituted by one or more carboxylic acid moieties.

The term "heteroatom" as used herein, by itself or as part of another group, means an oxygen atom ("O"), a sulfur atom ("S") or a nitrogen atom ("N"). It will be recognized that when the heteroatom is nitrogen, it may form an $NR_1R_2$ moiety, where $R_1$ and $R_2$ are, independently from one another, hydrogen or alkyl, or together with the nitrogen to which they are bound, form a saturated or unsaturated 5-, 6-, or 7-membered ring.

The term "styryl" as used herein, by itself or as part of another group, means a conjugated system comprising of two aryl moieties linked through at least one double bond.

The term "TAG" as used herein, by itself or as part of another group, means a moiety that can be directly detected by its own signal or indirectly detected through the signal of its binding or bonding partner optically or radioactively.

The term "dye" as used herein, by itself or as part of another group, means an aryl, a heteroaryl or a conjugated compound that has its longest absorption peak longer than 400 nm, or its longest fluorescence peak longer than 400 nm, or its longest luminescence peak longer than 400 nm.

The term "click or clickable" as used herein, by itself or as part of another group, means a moiety that can selectively react with another functional group. A click pair may be exemplified by azide/alkyne (including DBCO, OCT, ALO, DIBO, BARAC, DIFO, DIMAC, MOFO), azide/methyl 2-(diphenylphosphaneyl)benzoate, tetrazine/OCT, carbonyl/hydrazine or hydrazide, carbonyl/hydroxylamine, thiol/maleimide, dicysteine/2-phenyl-1,3,2-dithiarsolane, or diol/bornic acid etc. (See P. Thirumurugan, et al., Chem Rev, 2013, 113, 4905).

The term "sample" means an amount of a material that shows what the rest of the material is or should be like, e.g. a sample of biological, chemical, environmental material, e.g. a sample of a body tissue, a sample of food, a soil sample.

A biological sample may be exemplified by:
1. a sample comprising suspended cells and/or cells debris, e.g. blood sample, suspension of cloned cells, body tissue homogenate, etc.;
2. a sample comprising of intact or damaged cells of an animal body, a body tissue, smear or fluid or a sample of a tumor, e.g. a biopsy sample; it may be a fresh tissue sample or preserved tissue sample, e.g. a formalin fixed paraffin embedded tissue sample;
3. a sample comprising a living organism, e.g. a sample of a medium comprising an animal, plant, bacterium, fungi, etc.;
4. a sample comprising viral particles, debris thereof, or viral products, e.g., a body smear comprising viral nucleic acids, proteins, peptides, etc.;
5. a sample comprising a cell organelle(s);
6. a sample comprising natural or recombinant biological molecules, e.g. blood plasma sample, conditioned cell culture media, etc.

Examples of chemical samples include but not limited to samples of libraries of chemical compounds, e.g., peptide libraries. Examples of the environmental samples include, but not limited to soil, water or air samples and food samples.

The sample may in one embodiment be immnunobilized onto a solid support, such as a body tissue sample immobilized on a glass or plastic slide; a cell-free sample comprising biological molecules immobilized onto a nitrocellulose membrane. The term "solid support" means a piece of any solid water insoluble material, such as a nitrocellulose membrane, glass slide. The support may in one embodiment be a one-molecular layer thick membrane or be a multi-molecular layered piece of a material, such as plastic or glass. The target in this embodiment is immobilized on a surface of the support. In another embodiment the solid support may be a three-dimensional structure, such as a gel block or a mesh of fibers. In this embodiment the target is immobilized within the structure. In one embodiment, the solid support is a cellular membrane, such as the plasma membrane. The term "immobilized" means that a sample or target is not movable on or within the support or is movable to a very limited degree.

Examples of supports suitable for immobilizing the samples include but not limited to synthetic polymer supports, such as polystyrene, polypropylene, substituted polystyrene (e.g, aminated or carboxylated polystyrene); polyacrylamides; polyamides; polyvinylchloride; glass; agarose; nitrocellulose; nylon; polyvinylidenedifluoride; surface-modified nylon, etc. The invention relates to a solid support that is chemically inert under conditions described herein, which means the chosen support may not have any major influence on the results of detection by the method. Accordingly, any such inert support suitable for immobilizing a sample or target fitting the chosen assay format, e.g., for IHC, ELISA, blotting etc., may be selected.

A sample may be itself solid, e.g., a sample of formalin fixed solid tissue (i.e., not a blood sample) and/or paraffin embedded tissue sample, e.g., a formalin fixed paraffin embedded sample of a solid tumor, a sample of a skin, lever, breast, lung, etc. In this embodiment, the sample itself may be accounted as solid support comprising an immobilized target.

The term "target" means an object of interest (supposedly present in the sample) that can be characterized by particular physical and functional features. In the context of the invention, the term "target" relates to the whole pool of substantially similar entities of that object present in the sample, but not to every individual single unit of that object.

Targets of chemical and environmental samples may be different pollutants, toxins, warfare substances, members of molecular libraries, industrial noxious waste, etc. The target may be a part of a structure of a cell, e.g. a protein of the plasma membrane. In this embodiment, the cellular structure where the target is immobilized may be considered as a type of s solid support within context of the present invention.

The term "analyte" as used herein refers to a molecule that is to be detected by the methods described herein. The molecule can be a protein, glycoprotein, glycolipid, lipid, a nucleic acid, or a biochemical or chemical molecule as defined above. An analyte of interest can be an analyte which changes in abundance in a cell in a pathological state; in these embodiments, a signal obtained from the methods described herein can be correlated to the diagnosis, status, or prognosis of a disease. In other preferred embodiments, an analyte of interest is not a natural component of a cell, but can be expressed in the cell by recombinant DNA techniques well known to the skilled in the art.

The term "incubate, incubating or incubation" means that a sample or target or a complex of a target with a binding agent, is maintained in a medium for a period of time, e.g., in a medium comprising a particular reagent that specifically interacts with a target, or a binding agent that is capable of directly or indirectly binding to the target, etc. The period of time may vary from 10 seconds to 3 min or continues for a longer period of time, for example 5-10 min, 10-20 min, 20-40 min, 40-60 min, 1-2 hours, more than 2 hours or overnight. The incubating may be performed under different temperature conditions depending on different embodiments, e.g., the type of the target molecule to be detected or type of binding agent and/or reporter used for the detection, etc. The term "incubating" in some embodiments may be interchangeably used with the term "washing", which usually used in conditions when a sample is incubated in a medium that lacks specific binding agent and serves to remove particular agents from the sample. The invention in most embodiments relates to incubation times within a range of 10 seconds to 20 minutes.

The term "binding agent" designates a molecule that is capable of direct or indirect binding to a target. The term "directly" means that the binding agent has affinity to the target and is capable of specifically recognizing and interacting with the target and binding to it, wherein the term "indirectly" means that the binding agent does not have specific affinity to the target but has such affinity to a substance which is associated with the target and is capable of specifically binding to this substance. The binding agent which is capable of direct binding to a target is termed herein "first binding agent". The binding agent which is capable of indirect binding to a target is termed herein "second binding agent". The first binding agent is typically used to contact the sample. It may be comprised of any molecule which will specifically bind to the target supposedly present in the sample. The second binding agent may, for example, be any molecule that binds the first binding agent. There may be multiple binding agents involved in a single detection. The first, second and further binding agents may be the members of a specific binding pair. A number of different specific binding pairs are known in the art. These are the pairs of two different molecules which have mutual affinity for each other and are capable of specifically binding to each other. Members of specific binding pairs suitable for use in practicing the invention may be of the immune or non-immune type. Non-immune specific binding pairs include systems where the specifically binding to each other components share a mutual affinity for each other, but they are not antibodies.

Exemplary non-immune binding pairs are biotin-avidin or biotin-streptavidin, folic acid-folate binding protein, complementary nucleic acids, receptor-ligand, etc. The invention also includes non-immune binding pairs which form a covalent bond with each other. Exemplary covalent binding pairs include sulfhydryl reactive groups such as maleimides and haloacetyl derivatives and amine reactive groups such as isothiocyanates, succinimidyl esters, sulfonyl halides, and coupler dyes such as 3-methyl-2-benzothiazolinone hydrazone (MBTH) and 3-(dimethyl-amino)benzoic acid (DMAB), etc.

Immune specific binding pairs may be exemplified by antibody/antibody systems or hapten/anti-hapten antibody or antigen/antibody systems. In one embodiment the immune specific binding pair may be an antibody/antibody binding pair comprising two or more antibody molecules having affinity to each other, for example a primary antibody and secondary antibody pair, wherein the primary antibody represents a first binding agent and the secondary antibody represents a second binding agent, or an antibody system comprising 3 or 4, or more antibody members. In other embodiments the immune specific binding pair may be represented hapter/anti-hapten system. For example, the first binding agent may be represented by a molecule comprising a hapten, such as a hapten labeled primary antibody, and the second binding agent may be represented by an anti-hapten antibody.

The term "hapten" designates a small molecule which can be considered as an isolated epitope to which an antibody can be made, although the hapten alone will not induce an immune response if injected into an animal, it must be conjugated to a carrier (usually a protein). As haptens are small molecules, multiple copies of a hapten may be attached to a large molecule, e.g. a polymer molecule, such as protein, nucleotide, dextran, etc. Haptens may serve as convenient label molecules for assay formats where it is necessary or advantageous to amplify a signal. Thus, the bound multiple copies of a hapten provide for enhanced sensitivity, e.g. increased signal strength. Non-limited examples of suitable haptens include FITC, DNP, myc digoxigenin, nitrotyrosine biotin, avidin, strepavidin and anti-dye antibodies (e.g. rhodamine, fluorescein, dansyl, etc.).

The term "antibody", as used herein, designates an immunoglobulin or a part thereof, and includes any polypeptide comprising an antigen-binding site regardless of the source, method of production, and other characteristics. The term includes for example, polyclonal, monoclonal, monospecific, polyspecific, humanized, single-chain, chimeric, synthetic, recombinant, hybrid, mutated, and CDR-grafted antibodies. A part of an antibody can include any fragment which can still bind antigen, for example, a Fab, F(ab')$_2$, Fv, scFv. The origin of the antibody is defined by the genomic sequence irrespective of the method of production.

"Primary antibody", as used herein, refers to an antibody that specifically binds to an analyte or a target molecule of a sample. In certain embodiments the primary antibody may be polymerized. Primary antibodies may be derived from any warm-blooded species, e.g., mammals, birds.

"Secondary antibody", as used herein, refers to an antibody that has an antigen binding domain that specifically binds to the primary antibody, or a hapten deposited in the target site, or hapten linked directly or indirectly to a primary antibody or another binding agent.

"Tertiary antibody", as used herein, refers to an antibody that has an antigen binding domain that specifically binds to a secondary antibody or a hapten linked to a secondary antibody or a hapten linked to polymer conjugated to a secondary antibody, or hapten deposited in the target site.

Sometimes an antibody may function both as a secondary and a tertiary antibody. Antibodies used in the invention, including primary antibodies, secondary antibodies and tertiary antibodies, may be derived from any mammal species, e.g., a rat, a mouse, a goat, a guinea pig, a donkey, a rabbit, horse, lama, camel, or any avian species e.g., chicken, duck. "Derived from any mammal or avian species", as used herein, means that at least a part of the nucleic acid sequence encoding a particular antibody originated from the genomic sequence of a specific mammal, e.g., a rat, a mouse, a goat, or a rabbit or a specific bird e.g., chicken, duck. The antibody may be of any isotype, e.g., IgG, IgM, IgA, IgD, IgE or any subclass, e.g., IgG1, IgG2, IgG3, IgG4.

The term "peroxidase activity" relates to an enzymatic activity catalyzing a reaction of the form "ROOR'+ electron donor(2e$^-$)+2H$^+$→ROH+R'OH". An enzyme having the peroxidase activity is termed herein "peroxidase". For many peroxidases the optimal substrate is hydrogen peroxide, but others are more active with organic hydroperoxides such as organic peroxides. The nature of the electron donor is very dependent on the structure of the enzyme, e.g., Horseradish peroxidase (HRP, EC 1.11.1.7) can use a variety of organic compounds both as electron donors and acceptors. HRP has an accessible active site, and many compounds can reach the site of the reaction.

The term "enzyme complex" relates to a mixture of two or more substances comprising at least an enzyme conjugate. The substances bind together with certain specificity and affinity. Examples include biotin-avidin, primary antibody-secondary antibody, antibody-protein A, antibody-protein G, DNP-anti-DNP, FITC-anti-FITC etc.

DESCRIPTION OF THE PREFERRED EMBODIMENTS

Despite progress made towards CARD methods for use in detecting analytes, there remains a great need in the art for materials and methods that provide enhanced detection of analytes by enzymatic signal amplification. The variety of commercial tyramide products are available for performing IHC, FISH and other biological applications, the need still exists for methods and compositions which provide increased sensitivity in the detection of biological markers normally present at low levels in a sample, e.g., by IHC, FISH or flow cytometry. Increased sensitivity would be useful, in particular, when a condition or a disease is associated with a change in the amount of expression of biological markers as compared to normal. Although CARD has a relatively good sensitivity of detection of target molecules in samples compared to many other currently available methods, in particular methods for immunohistochemical detection of targets, the CARD method does not fully solve the common problems with other peroxidase-based method's, e.g., strong background staining, insufficient sensitivity and time consumption, which burden the method in cases of histological samples improperly proceeded prior the staining or those having a low level of target expression. It normally takes 1 to 3 hours at minimum to process a sample from the step of labeling of targets to detection of the label.

The present application is directed to styryl phenols useful for preparing optically detectable peroxidase substrates used for the detection, discrimination and quantification of biological targets and events.

In one aspect of the invention, the compounds of the invention may be described by Formula 1:

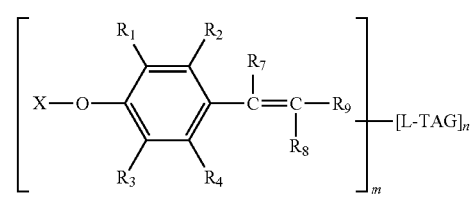

Formula 1

In this embodiment, $R_1$-$R_4$ are independently H, an alkyl, an alkenyl, an alkynyl, a halogen, carboxy, an alkoxy, an aryloxy, thiol, an alkylthiol, an arylthiol, azido, nitro, nitroso, cyano, an amino, hydroxy, a phosphonyl, a sulfonyl, a carbonyl, a boronyl, an aryl or a heteroaryl wherein $R_1$/$R_2$, $R_2$/$R_7$, or $R_4$/$R_7$ may optionally combine to form a 3-10 member ring; $R_7$ and $R_8$ are independently H, an alkyl, an alkenyl, an alkynyl, an alkoxy, an aryloxy, an alkylthiol, an arylthiol, an aryl or a heteroaryl wherein $R_7$/$R_8$ may combine to form a 3-10 member non-aromatic ring; $R_9$ is an aryl or a heteroaryl wherein $R_7$/$R_9$ or $R_8$/$R_9$ may optionally combine to form a 3-10 member non-aromatic ring; X is hydrogen, a counter cation or a moiety that can be cleaved by an enzyme, an ion, light, base or acid; L is a linker to connect the TAG moiety to the $R_1$ to $R_9$ positions; TAG is a biologically detectable moiety; m and n are independently an integer from 1 to 100 (e.g., from 1 to 5).

In another embodiment of the invention, $R_1$-$R_4$ are independently hydrogen, a halogen, an alkyl, or an alkoxy; $R_7$ and $R_8$ are independently H, an alkyl, an aryl, a heteroaryl; $R_9$ is an aryl or a heteroaryl; X is hydrogen, a caged group, a silyl ether, a phosphate, a sugar, an acyl, an alkyl, or arylmethyl; L is a chain of multiple intervening atoms that serves as a spacer to separate the TAG substance from the styryl phenol itself.

In another embodiment of the invention, the multiple styryl phenol moieties are randomly connected to multiple TAG moieties via. a group of different covalent bonds.

In another embodiment of the invention, the styryl phenol contains more than one TAG moieties, each of which is represented by -L-TAG where L is a covalent linkage attaching the TAG to the styryl phenol moiety.

In another embodiment of the invention, the styryl phenol moiety contains multiple TAGs that are represented by a group of different L-TAG moieties wherein $L_1$ is a covalent linkage attaching the first TAG to the styryl phenol moiety; $L_2$ is a covalent linkage attaching the second TAG to the same styryl phenol moiety, and so on.

The covalent linkage L is optionally a single covalent bond, such that the TAG is bound directly to the styryl phenol at any of the positions $R_1$-$R_9$, preferably at $R_9$. The linkage L is typically selected so as to link the styryl phenol to the TAG with stable chemical bonds, typically including carbon-carbon bonds, carbon-nitrogen bonds, nitrogen-nitrogen bonds, carbon-oxygen bonds and carbon-sulfur bonds. In addition to single, double, triple or aromatic carbon-carbon bonds, L typically includes ether, thioether, carboxamide, sulfonamide, urea, urethane or hydrazine functional moieties. Preferred L moieties have 1-20 nonhydrogen atoms selected from the group consisting of C, N, O and S. These preferred L moieties are composed of any combination of chemical bonds, including ether, thioether, amine, ester, carboxamide, sulfonamide, hydrazide bonds and aromatic or heteroaromatic bonds. Preferred L moieties are composed of any combination of single carbon-carbon bonds and carboxamide or thioether bonds. The longest linear segment of the linkage L preferably contains 4-10 nonhydrogen atoms including one or two heteroatoms.

Specific examples of L optionally include substituted or unsubstituted polymethylene, aryl, heteroaryl, arylene, alkylarylene or arylenealkyl. In another embodiment of the invention, L contains 1-6 carbon atoms. In another embodiment of the invention, L is a single covalent bond. In yet another embodiment of the invention, L has the formula —$(CH_2)_a(CONH(CH_2)_b)_z$, where a has any value from 0-10, b has any value from 1-10 and z is 0 to 5. In yet another embodiment of the invention, L is a thioether linkage. In yet another embodiment of the invention, L is a PEG linkage.

In another embodiment of the invention, the styryl phenol contains one TAG moiety that is represented by -L-TAG where L is optionally none, an alkyl, a PEG, an aryl, or a heteroaryl.

TAG moiety is a dye, a biotin, a click moiety, a hapten, a luminol, an acridinium ester, a ruthenium complex, a lanthanide complex, an antibody, an oligonucleotide, a DNA, an RNA, a fluorescent protein, a fluorescent conjugated polymer, a quantum dot, or a radioactive isotope.

The preferred dye TAG moieties are acridines, acridiniums, acridones, anthraquinones, azo dyes, azin dyes, phthalocyanines, Eurhodin dyes, safranins, indamins, indophenols, oxazines, thiazines, oxazoles, thiazoles, polythiophenes, polypyrroles, pyronins, pyryliums, fluoresceins, rhodamines, coumarins, cyanines, porphyrins, rhodols, quinolines, bodipy dyes, squaraines, perylenediimides, diketopyrrolopyrroles, conjugated polymers, fluorescent proteins, quantum dots, or polymer dots.

Specific examples of color dyes optionally include substituted or unsubstituted Alcian yellow GXS, Alizarin, Alizarin red S, Alizarin yellow GG, Alizarin yellow R, Azophloxin, Bismarck brown R, Bismarck brown Y, Brilliant cresyl blue, Chrysoidine R, Chrysoidine Y, Congo red, Crystal violet, Fuchsin acid, Gentian violet, Janus green, Lissamine fast yellow, Malachite green, Martius yellow, Meldola blue, Metanil yellow, Methyl orange, Methyl red, Naphthalene black 12B, Naphthol green B, Naphthol yellow S, Orange G, Purpurin, Rose Bengal, Sudan II, Titan yellow, Tropaeolin O, Tropaeolin OO, Tropaeolin OOO, Victoria blue 4R, Victoria blue B, Victoria blue R, Xylene cyanol FF, Acid Yellow 11, Acid Yellow 17, Acid Yellow 19, Acid Yellow 23, Acid Yellow 25, Acid Yellow 36, Acid Yellow 42, Acid Yellow 44, Acid Yellow 49, Acid Yellow 59, Acid Yellow 61, Acid Yellow 72, Acid Yellow 73, Acid Yellow 76, Acid Yellow 79, Acid Yellow 99, Acid Yellow 110, Acid Yellow 116, Acid Yellow 117, Acid Yellow 127, Acid Yellow 128, Acid Yellow 129, Acid Yellow 137, Acid Yellow 151, Acid Yellow 159, Acid Yellow 184, Acid Yellow 194, Acid Yellow 199, Acid Yellow 204, Acid Yellow 216, Acid Yellow 219, Acid Yellow 220, Acid Yellow 230, Acid Yellow 232, Acid Yellow 235, Acid Yellow 241, Acid Yellow 246, Acid Yellow 250, Acid Yellow 252, Acid Orange 3, Acid Orange 7, Acid Orange 8, Acid Orange 10, Acid Orange 24, Acid Orange 33, Acid Orange 51, Acid Orange 56, Acid Orange 60, Acid Orange 67, Acid Orange 74, Acid Orange 80, Acid Orange 86, Acid Orange 95, Acid Orange 107, Acid Orange 116, Acid Orange 142, Acid Orange 144, Acid Orange 154, Acid Orange 156, Acid Red 1, Acid Red 4, Acid Red 14, Acid Red 18, Acid Red 35, Acid Red 37, Acid Red 52, Acid Red 54, Acid Red 57, Acid Red 87, Acid Red 88, Acid Red 97, Acid Red 111, Acid Red 114, Acid Red 119, Acid Red 127, Acid Red 128, Acid Red 131, Acid Red 138, Acid Red 151, Acid Red 154, Acid Red 182, Acid Red 183, Acid Red 184, Acid Red 186, Acid Red 195, Acid Red 211, Acid Red 213, Acid Red 215, Acid Red 219, Acid Red 249, Acid Red 251, Acid Red 254, Acid Red 256, Acid Red 257, Acid Red 260, Acid Red 265, Acid Red 266, Acid Red 299, Acid Red 315, Acid Red 336, Acid Red 337, Acid Red 357, Acid Red 359, Acid Red 361, Acid Red 362, Acid Red 374, Acid Red 405, Acid Red 414, Acid Red 418, Acid Red 419, Acid Red 425, Acid Red 426, Acid Red 430, Acid Red 432, Acid Red 447, Acid Violet 1, Acid Violet 7, Acid Violet 12, Acid Violet 17, Acid Violet 43, Acid Violet 48, Acid Violet 49, Acid Violet 54, Acid Violet 58, Acid Violet 68, Acid Violet 90, Acid Blue 1, Acid Blue 7, Acid Blue 9, Acid Blue 15, Acid Blue 25, Acid Blue 40, Acid Blue 41, Acid Blue 45, Acid Blue 62, Acid Blue 74, Acid Blue 78, Acid Blue 80, Acid Blue 83, Acid Blue 90, Acid Blue 92, Acid Blue 93, Acid Blue 113, Acid Blue 120, Acid Blue 127, Acid Blue 129, Acid Blue 142, Acid Blue 145, Acid Blue 158, Acid Blue 171, Acid Blue 185, Acid Blue 193, Acid Blue 260, Acid Blue 264, Acid Blue 277, Acid Blue 280, Acid Blue 281, Acid Blue 284, Acid Blue 317, Acid Blue 324, Acid Blue 335, Acid Blue 350, Acid Green 1, Acid Green 9, Acid Green 12, Acid Green 16, Acid Green 25, Acid Green 27, Acid Green 28, Acid Green 41, Acid Green 43, Acid Green 68, Acid Green 68, Acid Green 73, Acid Green 80, Acid Green 104, Acid Green 111, Acid Green 114, Acid Brown 2, Acid Brown 14, Acid Brown 15, Acid Brown 21, Acid Brown 37, Acid Brown 48, Acid Brown 52, Acid Brown 58, Acid Brown 70, Acid Brown 78, Acid Brown 83, Acid Brown 85, Acid Brown 88, Acid Brown 97, Acid Brown 98, Acid Brown 100, Acid Brown 106, Acid Brown 112, Acid Brown 113, Acid Brown 121, Acid Brown 127, Acid Brown 160, Acid Brown 161, Acid Brown 165, Acid Brown 188, Acid Brown 189, Acid Brown 191, Acid Brown 213, Acid Brown 214, Acid Brown 235, Acid Brown 282, Acid Brown 283, Acid Brown 298, Acid Brown 314, Acid Brown 324, Acid Brown 332, Acid Brown 348, Acid Brown 349, Acid Brown 354, Acid Brown 355, Acid Brown 357, Acid Brown 365, Acid Brown 384, Acid Brown 402, Acid Brown 425, Acid Brown 434, Acid Brown 452, Acid Black 1, Acid Black 2, Acid Black 24, Acid Black 26, Acid Black 52, Acid Black 60, Acid Black 63, Acid Black 71, Acid Black 84, Acid Black 107, Acid Black 132, Acid Black 164, Acid Black 170, Acid Black 172, Acid Black 194, Acid Black 210, Acid Black 234, Acid Black 235, Direct Yellow 8, Direct Yellow 11, Direct Yellow 12, Direct Yellow 27, Direct Yellow 28, Direct Yellow 44, Direct Yellow 50, Direct Yellow 86, Direct Yellow 96, Direct Yellow 99, Direct Yellow 106, Direct Yellow 132, Direct Yellow 142, Direct Yellow 147, Direct Yellow 157, Direct Orange 26, Direct Orange 34, Direct Orange 37, Direct Orange 39, Direct Orange 102, Direct Orange 106, Direct Red 1, Direct Red 2, Direct Red 23, Direct Red 31, Direct Red 75, Direct Red 76, Direct Red 79, Direct Red 80, Direct Red 81, Direct Red 83, Direct Red 89, Direct Red 99, Direct Red 111, Direct Red 218, Direct Red 224, Direct Red 227, Direct Red 239, Direct Red 243, Direct Violet 7, Direct Violet 9, Direct Violet 48, Direct Violet 51, Direct Violet 66, Direct Blue 1, Direct Blue 15, Direct Blue 67, Direct Blue 71, Direct Blue 78, Direct Blue 80, Direct Blue 86, Direct Blue 106, Direct Blue 108, Direct Blue 151, Direct Blue 191, Direct Blue 199, Direct Blue 200, Direct Blue 201, Direct Blue 202, Direct Blue 218, Direct Blue 237, Direct Blue 290, Direct Green 1, Direct Green 26, Direct Green 28, Direct Green 89, Direct Green 96, Direct Brown 103, Direct Brown 115, Direct Brown 116, Direct Brown 210, Direct Black 19, Direct Black 22, Direct Black 32, Direct Black 51, Direct Black 56, Direct Black 62, Direct Black 80, Direct Black 112, Direct Black 155, Direct Black 166, Direct Black 168, Direct Black 173, Direct Black 178, Direct Black 184, Disperse Yellow 3, Disperse Yellow 23, Disperse Yellow 42, Disperse Yellow 54, Disperse Yellow 56, Disperse Yellow 64, Disperse Yellow 82, Disperse Yellow 114, Disperse yellow 119, Disperse Yellow 124, Disperse Yellow 184:1, Disperse Yellow 198, Disperse Yellow 211, Disperse Yellow 229, Disperse Yellow 236, Disperse Yellow 241, Disperse Orange 3, Disperse Orange 25, Disperse Orange 29, Disperse Orange 30, Disperse Orange 37, Disperse Orange 44, Disperse Orange 61, Disperse Orange 67, Disperse Orange 73, Disperse Orange 76, Disperse Red 1, Disperse Red 4, Disperse Red 5, Disperse Red 11, Disperse Red 13, Disperse Red 17, Disperse Red 50, Disperse Red 54, Disperse Red 60, Disperse Red 65, Disperse Red 72, Disperse Red 73, Disperse Red 74, Disperse Red 82, Disperse Red 91, Disperse Red 92, Disperse Red 118, Disperse Red 135, Disperse Red 153, Disperse Red 167, Disperse Red 167:1, Disperse Red 177, Disperse Red 179, Disperse Red 194, Disperse Red 202, Disperse Red 277, Disperse Red 319, Disperse Red 324, Disperse Red 343, Disperse Red 363, Disperse Violet 1, Disperse Violet 8, Disperse Violet 26, Disperse Violet 28, Disperse Violet 33, Disperse Violet 63, Disperse Violet 93, Disperse Blue 3, Disperse Blue 35, Disperse Blue 56, Disperse Blue 60, Disperse Blue 73, Disperse Blue 79, Disperse Blue 79:1, Disperse Blue 85, Disperse Blue 87, Disperse Blue 94, Disperse Blue 102, Disperse Blue 106, Disperse Blue 148, Disperse Blue 165, Disperse Blue 183, Disperse Blue 281, Disperse Blue 291, Disperse Brown 1, Mordant Yellow 1, Mordant Yellow 8, Mordant Yellow 10, Mordant Orange 1, Mordant Orange 3, Mordant Red 7, Mordant Red 9, Mordant Red 19, Mordant Blue 1, Mordant Blue 3, Mordant Blue 13, Mordant Brown 15, Mordant Brown 33, Mordant Black 9, Mordant Black 11, Mordant Black 13, Mordant Black 17, Reactive Yellow 7, Reactive Yellow 15, Reactive Yellow 17, Reactive Yellow 18, Reactive Yellow 22, Reactive Yellow 24, Reactive Yellow 37, Reactive Yellow 39, Reactive Yellow 42, Reactive Yellow 44, Reactive Yellow 57, Reactive Yellow 81, Reactive Yellow 84, Reactive Yellow 85, Reactive Yellow 86, Reactive Yellow 105, Reactive Yellow 135, Reactive Yellow 145, Reactive Yellow 160A, Reactive Yellow 160, Reactive Yellow 167, Reactive Yellow 176, Reactive Orange 1, Reactive Orange 4, Reactive Orange 5, Reactive Orange 12, Reactive Orange 13, Reactive Orange 14, Reactive Orange 16, Reactive Orange 20, Reactive Orange 84, Reactive Orange 96, Reactive Orange 107, Reactive Orange 122, Reactive Red 2, Reactive Red 3, Reactive Red 11, Reactive Red 21, Reactive Red 24, Reactive Red 29, Reactive Red 31, Reactive Red 35, Reactive Red 43, Reactive Red 45, Reactive Red 65, Reactive Red 66, Reactive Red 76, Reactive Red 83, Reactive Red 84, Reactive Red 106, Reactive Red 120, Reactive Red 136, Reactive Red 141, Reactive Red 152, Reactive Red 170, Reactive Red 174, Reactive Red 180, Reactive Red 195, Reactive Red 198, Reactive Violet 1, Reactive Violet 5, Reactive Blue 3, Reactive Blue 4, Reactive Blue 5, Reactive Blue 7, Reactive Blue 9, Reactive Blue 13, Reactive Blue 19, Reactive Blue 21, Reactive Blue 25, Reactive Blue 28, Reactive Blue 38, Reactive Blue 50, Reactive Blue 69, Reactive Blue 71, Reactive Blue 89, Reactive Blue 109, Reactive Blue 140, Reactive Blue 160, Reactive Blue 168, Reactive Blue 171, Reactive Blue 194, Reactive Blue 198, Reactive Blue 203, Reactive Blue 220, Reactive Blue 221, Reactive Blue 222, Reactive Blue 231, Reactive Blue 250, Reactive Blue-, Reactive Green 19A, Reactive Green 19, Reactive Brown 9, Reactive Brown 18, Reactive Black 5, Solvent Yellow 2, Solvent Yellow 14, Solvent Yellow 16, Solvent Yellow 18, Solvent Yellow 19, Solvent Yellow 21, Solvent Yellow 29, Solvent Yellow 33, Solvent Yellow 43, Solvent Yellow 44, Solvent Yellow 47, Solvent Yellow 56, Solvent Yellow 62, Solvent Yellow 72, Solvent Yellow 79, Solvent Yellow 82, Solvent Yellow 88, Solvent Yellow 90, Solvent Yellow 93, Solvent Yellow 94, Solvent Yellow 98, Solvent Yellow 104, Solvent Yellow 114, Solvent Yellow 135, Solvent Yellow 141, Solvent Yellow 145, Solvent Yellow 146, Solvent Yellow 157, Solvent Yellow 160:1, Solvent Yellow 163, Solvent Yellow 172, Solvent Yellow 176, Solvent Yellow 179, Solvent Orange 2, Solvent Orange 3, Solvent Orange 7, Solvent Orange 11, Solvent Orange 45, Solvent Orange 54, Solvent Orange 56, Solvent Orange 58, Solvent Blue 5, Solvent Blue 6, Solvent Blue 11, Solvent Blue 23, Solvent Blue 26, Solvent Blue 35, Solvent Blue 36, Solvent Blue 38, Solvent Blue 45, Solvent Blue 48, Solvent Blue 58, Solvent Blue 59, Solvent Blue 63, Solvent Blue 67, Solvent Blue 70, Solvent Blue 78, Solvent Blue 94, Solvent Blue 97, Solvent Blue 101, Solvent Blue 104, Solvent Blue 122, Solvent Blue 128, Solvent Blue 132, Solvent Green 1, Solvent Green 3, Solvent Green 5, Solvent Green 7, Solvent Green 28, Solvent Brown 5, Solvent Brown 20, Solvent Brown 41, Solvent Brown 43, Solvent Brown 53, Solvent Brown 58, Solvent Black 3, Solvent Black 5, Solvent Black 7, Solvent Black 27, Solvent Black 29, or Solvent Black 34.

Specific examples of fluorescent dyes optionally include substituted or unsubstituted ATTO 465, ATTO 488, ATTO 495, ATTO 514, ATTO 532, ATTO 550, ATTO 565, ATTO 590, ATTO 594, ATTO 610, ATTO 620, ATTO 633, ATTO 647, ATTO 647N, ATTO 655, ATTO 665, ATTO 680, ATTO 700, ATTO 725, ATTO 740, 5-carboxy-2,7-dichlorofluorescein, 5-FAM, 5-Carboxynapthofluorescein, 5-ROX, 6-TAMRA, 6-Carboxyrhodamine 6G, 6-JOE, 6-FAM, 6-ROX, Alexa Fluor 488, Alexa Fluor 532, Alexa Fluor 546, Alexa Fluor 568, Alexa Fluor 594, Alexa Fluor 633, Alexa Fluor 647, Alexa Fluor 660, Alexa Fluor 680, Bodipy 492/515, Bodipy 493/503, Bodipy 500/510, Bodipy 505/515, Bodipy 530/550, Bodipy 542/563, Bodipy 558/568, Bodipy 564/570, Bodipy 576/589, Bodipy 581/591, Bodipy 630/650-X, Bodipy 650/665-X, Bodipy 665/676, Bodipy Fl, Bodipy R6G SE, Bodipy TMR, Bodipy TR, CF 488A, CF 555, CF 568, CF 594, CF 633, CF 640R, CF 647, CF 660C, CF 680, CF680R, CF 750, CF 770, CF 790, CL-NERF, CMFDA, Cy2, Cy3, Cy3.5, Cy5, Cy5.5, Cy7, DDAO, DiA, DiD, DiI, DyLight 488, DyLight 550, DyLight 594, DyLight 633, DyLight 650, DyLight 680, DyLight 755, DyLight 800, DiO, DiR, DM-NERF, DsRed, DTAF, DY-490, DY-495, DY-505, DY-530, DY-547, DY-548, DY-549, DY-549P1, DY-550, DY-554, DY-555, DY-556, DY-560, DY-590, DY-591, DY-594, DY-605, DY-610, DY-615, DY-630, DY-631, DY-632, DY-633, DY-634, DY-635, DY-636, DY-647, DY-648, DY-649, DY-649P1, DY-650, DY-651, DY-652, DY-654, DY-675, DY-676, DY-677, DY-678, DY-679, DY-679P1, DY-680, DY-681, DY-682, DY-700, DY-701, DY-703, DY-704, DY-730, DY-731, DY-732, DY-734, DY-749, DY-750, DY-751, DY-752, DY-754, DY-776, DY-777, DY-778, DY-780, DY-781, DY-782, DY-800, DY-831, Eosin, Erythrosin, FITC, Fluo-3, Fluo-4, Fluor-Ruby, FluorX, FM 1-43, FM 4-46, iFluor 488, iFluor 555, iFluor 594, iFluor 647, iFluor 680, iFluor 700, iFluor 750, iFluor 780, Lyso Tracker Green, Lyso Tracker Yellow, Mitotracker Green, Mitotracker Orange, Mitotracker Red, NBD, Oregon Green 488, Oregon Green 514, PKH26, PKH67, Resorufin, GFP, YFP, RFP, PE, APC, PerCP, Brilliant Violet 421, Brilliant Violet 510, Brilliant Violet 570, Brilliant Violet 605, Brilliant Violet 650, Brilliant Violet 711, Brilliant Violet 750, Brilliant Violet 785, BUV 395, BUV496, BUV737, SuperBright 436, SuperBright 600, SuperBright 645, SuperBright 702, or SuperBright 780.

Specific examples of aryl ring systems include substituted or unsubstituted phenyl, biphenyl, naphthyl, anthryl, phenanthrenyl or pyrenyl.

Specific examples of heteroaryl ring systems include substituted or unsubstituted thienyl, benzothienyl, naphthothienyl, furyl, pyranyl, isobenzofuranyl, benzoxazolyl, chromenyl, xanthenyl, phenoxathiinyl, pyrrolyl, imidazolyl, pyrazolyl, pyridyl, pyrazinyl, pyrimidinyl, indolyl, purinyl, quinolyl, phthalazinyl, naphthyridinyl, quinazolinyl, cinnolinyl, carbazolyl, phenanthridinyl, acridinyl, phenazinyl, thiazolyl, oxazolyl, furazanyl, phenoxazinyl, or tetrazolyl.

In one aspect of the invention, the compounds of the invention may be described by Formula 2:

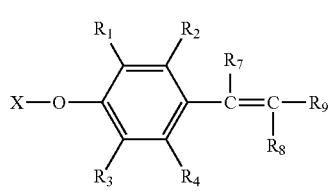

Formula 2

In this embodiment, $R_1$-$R_4$ are independently H, an alkyl, an alkenyl, an alkynyl, a halogen, carboxy, an alkoxy, an aryloxy, thiol, an alkylthiol, an arylthiol, azido, nitro, nitroso, cyano, an amino, hydroxy, a phosphonyl, a sulfonyl, a carbonyl, a boronyl, an aryl, a heteroaryl, or [L-TAG]n wherein $R_1/R_2$, $R_2/R_7$, or $R_4/R_7$ may optionally combine to form a 3-10 member ring; $R_7$ and $R_8$ are independently H, an alkyl, an alkenyl, an alkynyl, an alkoxy, an aryloxy, an alkylthiol, an arylthiol, an aryl, a heteroaryl or [L-TAG]$_n$ wherein $R_7/R_8$ may combine to form a 3-10 member non-aromatic ring; $R_9$ is an aryl, a heteroaryl or [L-TAG]$_n$ wherein $R_7/R_9$ or $R_8/R_9$ may optionally combine to form a 3-10 member non-aromatic ring; X is hydrogen, a counter cation or a moiety that can be cleaved by an enzyme, an ion, light, base or acid; L is a linker; TAG is a biologically detectable moiety; n is an integer from 1 to 100 (e.g., from 1 to 5).

In another embodiment, $R_1$, $R_2$ and $R_4$ are H; $R_3$ is H, an alkyl, an alkenyl, an alkynyl, a halogen, carboxy, an alkoxy, an aryloxy, thiol, an alkylthiol, an arylthiol, azido, nitro, nitroso, cyano, an amino, hydroxy, a phosphonyl, a sulfonyl, a carbonyl, a boronyl, an aryl, a heteroaryl, or [L-TAG]n wherein $R_1/R_2$, $R_2/R_7$, or $R_4/R_7$ may optionally combine to form a 3-10 member ring; $R_7$ and $R_8$ are independently H, an alkyl, an alkenyl, an alkynyl, an alkoxy, an aryloxy, an alkylthiol, an arylthiol, an aryl, a heteroaryl or [L-TAG]n wherein $R_7/R_8$ may combine to form a 3-10 member non-aromatic ring; $R_9$ is an aryl, a heteroaryl or [L-TAG]n wherein $R_7/R_9$ or $R_8/R_9$ may optionally combine to form a 3-10 member non-aromatic ring; X is hydrogen, a counter cation or a moiety that can be cleaved by an enzyme, an ion, light, base or acid; L is a linker; TAG is a biologically detectable moiety; n is an integer selected from the integers 1, 2, 3, 4 and 5.

In one aspect of the invention, the compounds of the invention may be described by Formula 3:

Formula 3

In this embodiment, $R_1$-$R_4$ and $R_{10}$-$R_{14}$ are independently H, an alkyl, a halogen, carboxy, an alkoxy, an aryloxy, thiol, an alkylthiol, an arylthiol, azido, nitro, nitroso, cyano, an amino, hydroxy, a phosphonyl, a sulfonyl, a carbonyl, a boronyl, an aryl, a heteroaryl or [L-TAG]$_n$ wherein $R_1/R_2$, $R_2/R_7$, $R_4/R_7$, $R_7/R_{10}$, $R_7/R_{14}$, $R_8/R_{10}$, $R_8/R_{14}$, $R_{10}/R_{11}$, $R_{11}/R_{12}$, $R_{12}/R_{13}$, or $R_{13}/R_{14}$ may optionally form a 3-10 member ring; $R_7$ and $R_8$ are independently H, an alkyl, an alkenyl, an alkynyl, an alkoxy, an aryloxy, an alkylthiol, an arylthiol, an aryl, a heteroaryl or [L-TAG]$_n$ wherein $R_7/R_8$ may optionally form a non-aromatic 3-10 member ring; X is hydrogen, a counter cation or a moiety that can be cleaved by an enzyme, an ion, light, base or acid; L is a linker; TAG is a dye, a biotin, FITC, DNP, DIG, a luminol, an acridinium ester, a ruthenium complex, an europium complex, a terbium complex, a fluorescent protein, a fluorescent conjugated polymer, or a quantum dot; n is an integer from 1 to 100 (e.g., from 1 to 5).

In another embodiment of the invention, $R_1$-$R_4$ are independently hydrogen, a halogen, an alkyl, or an alkoxy; $R_7$-$R_{14}$ are independently H, an alkyl, an aryl, or a heteroaryl; X is hydrogen, a caged group, a silyl ether, a phosphate, a sugar, an acyl, an alkyl, or arylmethyl; L is a chain of multiple intervening atoms that serves as a spacer to separate the TAG substance from the styryl phenol itself.

In another embodiment of the invention, TAG is an acridine, acridinium ester, an acridone, an anthraquinone, an azo dye, a phthalocyanine, an oxazine, a thiazine, an oxazole, a thiazole, a fluorescein, a rhodamine, a coumarin, a cyanine, a porphyrin, a rhodol, a bodipy, a squaraine, a perylenediimide, a diketopyrrolopyrrole, a conjugated polymer, a fluorescent protein, a quantum dot, or a polymer dot.

In another embodiment of the invention, TAG is ATTO 465, ATTO 488, ATTO 495, ATTO 514, ATTO 532, ATTO 550, ATTO 565, ATTO 590, ATTO 594, ATTO 610, ATTO 620, ATTO 633, ATTO 647, ATTO 647N, ATTO 655, ATTO 665, ATTO 680, ATTO 700, ATTO 725, ATTO 740, 5-carboxy-2,7-dichlorofluorescein, 5-FAM, 5-Carboxynaptho-fluorescein, 5-ROX, 6-TAMRA, 6-Carboxyrhodamine 6G, 6-JOE, 6-FAM, 6-ROX, Alexa Fluor 488, Alexa Fluor 532, Alexa Fluor 546, Alexa Fluor 568, Alexa Fluor 594, Alexa Fluor 633, Alexa Fluor 647, Alexa Fluor 660, Alexa Fluor 680, Bodipy 492/515, Bodipy 493/503, Bodipy 500/510, Bodipy 505/515, Bodipy 530/550, Bodipy 542/563, Bodipy 558/568, Bodipy 564/570, Bodipy 576/589, Bodipy 581/591, Bodipy 630/650-X, Bodipy 650/665-X, Bodipy 665/676, Bodipy Fl, Bodipy R6G SE, Bodipy TMR, Bodipy TR, CF 488A, CF 555, CF 568, CF 594, CF 633, CF 640R, CF 647, CF 660C, CF 680, CF680R, CF 750, CF 770, CF 790, CL-NERF, CMFDA, Cy2, Cy3, Cy3.5, Cy5, Cy5.5, Cy7, DDAO, DiA, DiD, DiI, DyLight 488, DyLight 550, DyLight 594, DyLight 633, DyLight 650, DyLight 680, DyLight 755, DyLight 800, DiO, DiR, DM-NERF, DsRed, DTAF, DY-490, DY-495, DY-505, DY-530, DY-547, DY-548, DY-549, DY-549P1, DY-550, DY-554, DY-555, DY-556, DY-560, DY-590, DY-591, DY-594, DY-605, DY-610, DY-615, DY-630, DY-631, DY-632, DY-633, DY-634, DY-635, DY-636, DY-647, DY-648, DY-649, DY-649P1, DY-650, DY-651, DY-652, DY-654, DY-675, DY-676, DY-677, DY-678, DY-679, DY-679P1, DY-680, DY-681, DY-682, DY-700, DY-701, DY-703, DY-704, DY-730, DY-731, DY-732, DY-734, DY-749, DY-750, DY-751, DY-752, DY-754, DY-776, DY-777, DY-778, DY-780, DY-781, DY-782, DY-800, DY-831, Eosin, Erythrosin, FITC, Fluo-3, Fluo-4, Fluor-Ruby, FluorX, FM 1-43, FM 4-46, iFluor 488, iFluor 555, iFluor 594, iFluor 647, iFluor 680, iFluor 700, iFluor 750, iFluor 780, Lyso Tracker Green, Lyso Tracker Yellow, Mitotracker Green, Mitotracker Orange, Mitotracker Red, NBD, Oregon Green 488, Oregon Green 514, PKH26, PKH67, Resorufin, GFP, YFP, RFP, PE, APC, PerCP, Brilliant Violet 421, Brilliant Violet 510, Brilliant Violet 570, Brilliant Violet 605, Brilliant Violet 650, Brilliant Violet 711, Brilliant Violet 750, Brilliant Violet 785, BUV 395, BUV496, BUV737, SuperBright 436, SuperBright 600, SuperBright 645, SuperBright 702, or SuperBright 780.

In one aspect of the invention, the compounds of the invention may be described by Formula 4:

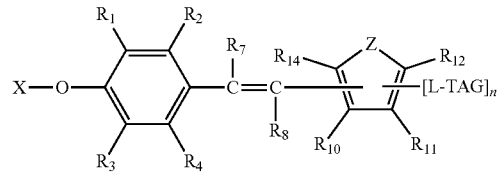

Formula 4

In this embodiment, $R_1$-$R_4$ and $R_{10}$-$R_{14}$ are independently H, an alkyl, a halogen, carboxy, an alkoxy, an aryloxy, thiol, an alkylthiol, an arylthiol, azido, nitro, nitroso, cyano, an amino, hydroxy, a phosphonyl, a sulfonyl, a carbonyl, a boronyl, an aryl or a heteroaryl wherein $R_1/R_2$, $R_2/R_7$, $R_4/R_7$, $R_7/R_{10}$, $R_7/R_{14}$, $R_8/R_{10}$, $R_8/R_{14}$, $R_{10}/R_{11}$, $R_{11}/R_{12}$, or $R_{10}/R_{14}$ may optionally form a 3-10 member ring; $R_7$ and $R_8$ are independently H, an alkyl, an alkenyl, an alkynyl, an alkoxy, an aryloxy, an alkylthiol, an arylthiol, an aryl or a heteroaryl wherein $R_7/R_8$ may optionally form a non-aromatic 3-10 member ring; X is hydrogen, a counter cation or a moiety that can be cleaved by an enzyme, an ion, light, base or acid; L is a linker to connect TAG moiety to the $R_1$ to $R_{14}$ positions; TAG is a dye, a biotin, FITC, DNP, DIG, a luminol, an acridinium ester, a ruthenium complex, an europium complex, a terbium complex, a fluorescent protein, a fluorescent conjugated polymer, a quantum dot, or a radioactive isotope; Z is O, S, NR$_{15}$, or C(R$_{16}$)=NR$_{15}$ wherein $R_{15}$ and $R_{16}$ are independently hydrogen, an alkyl, an alkenyl, an alkynyl, an aryl, or an heteroaryl; n is an integer from 1 to 100 (e.g., from 1 to 5).

In another embodiment of the invention, $R_1$-$R_4$ are independently hydrogen, a halogen, an alkyl, or an alkoxy; $R_7$-$R_{14}$ are independently H, an alkyl, an aryl, or a heteroaryl; X is hydrogen, a caged group, a silyl ether, a phosphate, a sugar, an acyl, an alkyl, or arylmethyl; L is a chain of multiple intervening atoms that serves as a spacer to separate the TAG substance from the styryl phenol itself.

In another embodiment of the invention, $R_1$-$R_4$ are independently hydrogen, a halogen, an alkyl, or an alkoxy; $R_7$-$R_{14}$ are independently H, an alkyl, an aryl, or a heteroaryl; X is hydrogen, a caged group, a silyl ether, a phosphate, a sugar, an acyl, an alkyl, or arylmethyl; L is a chain of multiple intervening atoms that serves as a spacer to separate the TAG substance from the styryl phenol itself; TAG is a dye, a biotin, DNP, DIG, a fluorescent protein, a fluorescent conjugated polymer or a quantum dot; Z is O, S, or NH.

In another embodiment of the invention, TAG is an azo dye, a phthalocyanine, an oxazine, a thiazine, an oxazole, a thiazole, a fluorescein, a rhodamine, a coumarin, a cyanine, a porphyrin, a rhodol, a bodipy, a squaraine, a perylenediimide, a diketopyrrolopyrrole, a conjugated polymer, or a fluorescent protein.

In one aspect of the invention, the compounds of the invention may be described by Formula 5:

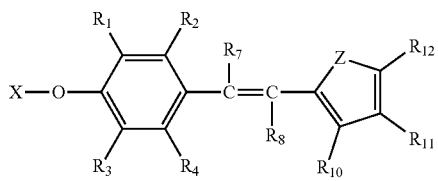

Formula 5

In this embodiment, $R_1$-$R_4$ and $R_{10}$-$R_{12}$ are independently H, an alkyl, a halogen, carboxy, an alkoxy, an aryloxy, thiol, an alkylthiol, an arylthiol, azido, nitro, nitroso, cyano, an amino, hydroxy, a phosphonyl, a sulfonyl, a carbonyl, a boronyl, an aryl, a heteroaryl or [L-TAG]$_n$ wherein $R_1/R_2$, $R_2/R_7$, $R_4/R_7$, $R_7/R_{10}$, $R_7/R_{14}$, $R_8/R_{10}$, $R_8/R_{14}$, $R_{10}/R_{11}$, $R_{11}/R_{12}$, or $R_{10}/R_{14}$ may optionally form a 3-10 member ring; $R_7$ and $R_8$ are independently H, an alkyl, an alkenyl, an alkynyl, an alkoxy, an aryloxy, an alkylthiol, an arylthiol, an aryl, a heteroaryl or [L-TAG]$_n$ wherein $R_7/R_8$ may optionally form a non-aromatic 3-10 member ring; X is hydrogen, a counter cation or a moiety that can be cleaved by an enzyme, an ion, light, base or acid; L is a linker; TAG is a dye, a biotin, FITC, DNP, DIG, a luminol, an acridinium ester, a ruthenium complex, an europium complex, a terbium complex, a fluorescent protein, a fluorescent conjugated polymer, a quantum dot, or a radioactive isotope; Z is O, S, $NR_{15}$, or $C(R_{16})$=$NR_{15}$ wherein $R_{15}$ and $R_{16}$ are independently hydrogen, an alkyl, an alkenyl, an alkynyl, an aryl, or an heteroaryl; n is an integer from 1 to 100 (e.g., from 1 to 5).

In one embodiment, $R_1$, $R_2$ and $R_4$ are H; $R_3$ and $R_{10}$-$R_{12}$ are independently an H, an alkyl, a halogen, carboxy, an alkoxy, an aryloxy, thiol, an alkylthiol, an arylthiol, azido, nitro, nitroso, cyano, an amino, hydroxy, a phosphonyl, a sulfonyl, a carbonyl, a boronyl, an aryl, a heteroaryl or [L-TAG] wherein $R_1/R_2$, $R_2/R_7$, $R_4/R_7$, $R_7/R_{10}$, $R_7/R_{14}$, $R_8/R_{10}$, $R_8/R_{14}$, $R_{10}/R_{11}$, $R_{11}/R_{12}$, or $R_{10}/R_{14}$ may optionally form a 3-10 member ring; $R_7$ and $R_8$ are independently H, an alkyl, an alkenyl, an alkoxy, an aryloxy, an alkylthiol, an arylthiol, an aryl, a heteroaryl or [L-TAG] wherein $R_7/R_8$ may optionally form a non-aromatic 3-10 member ring; X is hydrogen, a counter cation or a moiety that can be cleaved by an enzyme, an ion, light, base or acid; L is a linker; TAG is a dye, a biotin, FITC, DNP, DIG, a luminol, an acridinium ester, a ruthenium complex, an europium complex, a terbium complex, a fluorescent protein, a fluorescent conjugated polymer, a quantum dot, or a radioactive isotope; Z is O, S, $NR_{15}$, or $C(R_{16})$=$NR_{15}$ wherein $R_{15}$ and $R_{16}$ are independently hydrogen, an alkyl, an alkenyl, an alkynyl, an aryl, or an heteroaryl; n is an integer from 1 to 5.

In one aspect of the invention, the compounds of the invention may be described by Formula 6:

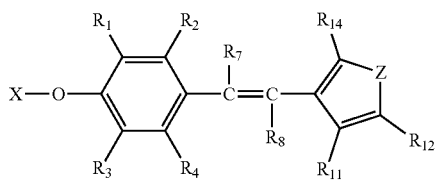

Formula 6

In this embodiment, $R_1$-$R_4$ and $R_{11}$, $R_{12}$ and $R_{14}$ are independently H, an alkyl, a halogen, carboxy, an alkoxy, an aryloxy, thiol, an alkylthiol, an arylthiol, azido, nitro, nitroso, cyano, an amino, hydroxy, a phosphonyl, a sulfonyl, a carbonyl, a boronyl, an aryl, a heteroaryl or [L-TAG]$_n$ wherein $R_1/R_2$, $R_2/R_7$, $R_4/R_7$, $R_7/R_{10}$, $R_7/R_{14}$, $R_8/R_{10}$, $R_8/R_{14}$, $R_{10}/R_{11}$, $R_{11}/R_{12}$, or $R_{10}/R_4$ may optionally form a 3-10 member ring; $R_7$ and $R_8$ are independently H, an alkyl, an alkenyl, an alkynyl, an alkoxy, an aryloxy, an alkylthiol, an arylthiol, an aryl, a heteroaryl or [L-TAG]$_n$ wherein $R_7/R_8$ may optionally form a non-aromatic 3-10 member ring; X is hydrogen, a counter cation or a moiety that can be cleaved by an enzyme, an ion, light, base or acid; L is a linker; TAG is a dye, a biotin, FITC, DNP, DIG, a luminol, an acridinium ester, a ruthenium complex, an europium complex, a terbium complex, a fluorescent protein, a fluorescent conjugated polymer, a quantum dot, or a radioactive isotope; Z is O, S, $NR_{15}$, or $C(R_{16})$=$NR_{15}$ wherein $R_{15}$ and $R_{16}$ are independently hydrogen, an alkyl, an alkenyl, an alkynyl, an aryl, or an heteroaryl; n is an integer from 1 to 100 (e.g., from 1 to 5).

In one embodiment, $R_1$, $R_2$ and $R_4$ are H; $R_3$ and $R_{11}$, $R_{12}$ and $R_{14}$ are independently an H, an alkyl, a halogen, carboxy, an alkoxy, an aryloxy, thiol, an alkylthiol, an arylthiol, azido, nitro, nitroso, cyano, an amino, hydroxy, a phosphonyl, a sulfonyl, a carbonyl, a boronyl, an aryl, a heteroaryl or [L-TAG]$_n$ wherein $R_1/R_2$, $R_2/R_7$, $R_4/R_7$, $R_7/R_{10}$, $R_7/R_{14}$, $R_8/R_{10}$, $R_8/R_{14}$, $R_{10}/R_{11}$, $R_{11}/R_{12}$, or $R_{10}/R_{14}$ may optionally form a 3-10 member ring; $R_7$ and $R_8$ are independently H, an alkyl, an alkenyl, an alkynyl, an alkoxy, an aryloxy, an alkylthiol, an arylthiol, an aryl, a heteroaryl or [L-TAG]$_n$ wherein $R_7/R_8$ may optionally form a non-aromatic 3-10 member ring; X is hydrogen, a counter cation or a moiety that can be cleaved by an enzyme, an ion, light, base or acid; L is a linker; TAG is a dye, a biotin, FITC, DNP, DIG, a luminol, an acridinium ester, a ruthenium complex, an europium complex, a terbium complex, a fluorescent protein, a fluorescent conjugated polymer, a quantum dot, or a radioactive isotope; Z is O, S, $NR_{15}$, or $C(R_{16})$=$NR_5$ wherein $R_{15}$ and $R_{16}$ are independently hydrogen, an alkyl, an alkenyl, an alkynyl, an aryl, or an heteroaryl; n is an integer from 1 to 5.

The present invention relates to methods and compounds for detection of molecular targets, such as biological or chemical molecules, or molecular structures, in samples using a host of experimental schemes for detecting and visualizing such targets, such as immunohistochemistry (IHC), in situ hybridization (ISH), ELISA, Southern, Northern, and Western blotting.

In one aspect of the invention, the compounds of Formula 1 may be used for biological detections in combination with a peroxidase conjugate and a peroxide compound.

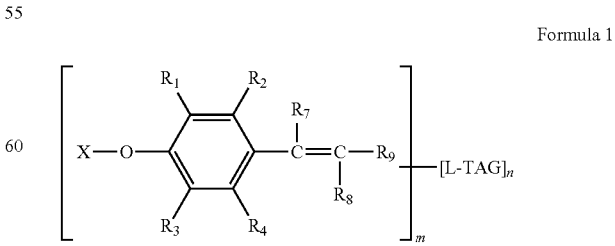

Formula 1

In this embodiment, $R_1$-$R_4$ are independently H, an alkyl, an alkenyl, an alkynyl, a halogen, carboxy, an alkoxy, an aryloxy, thiol, an alkylthiol, an arylthiol, azido, nitro, nitroso, cyano, an amino, hydroxy, a phosphonyl, a sulfonyl, a carbonyl, a boronyl, an aryl or a heteroaryl wherein $R_1/R_2$, $R_2/R_7$, or $R_4/R_7$ may optionally combine to form a 3-10 member ring; $R_7$ and $R_8$ are independently H, an alkyl, an alkenyl, an alkynyl, an alkoxy, an aryloxy, an alkylthiol, an arylthiol, an aryl or a heteroaryl wherein $R_7/R_8$ may combine to form a 3-10 member non-aromatic ring; $R_9$ is an aryl or a heteroaryl wherein $R_7/R_9$ or $R_8/R_9$ may optionally combine to form a 3-10 member non-aromatic ring; X is hydrogen, a counter cation or a moiety that can be cleaved by an enzyme, an ion, light, base or acid; L is a linker to connect the TAG moiety to the $R_1$ to $R_9$ positions; TAG is a biologically detectable moiety; m and n are independently an integer from 1 to 100 (e.g., from 1 to 5). In one aspect of the invention, the compounds of Formula 2 may be used for biological detections in combination with a peroxidase conjugate and a peroxide compound.

Formula 2

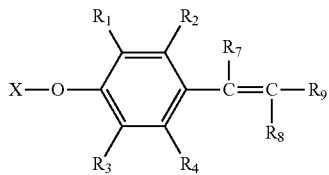

In this embodiment, $R_1$-$R_4$ are independently H, an alkyl, an alkenyl, an alkynyl, a halogen, carboxy, an alkoxy, an aryloxy, thiol, an alkylthiol, an arylthiol, azido, nitro, nitroso, cyano, an amino, hydroxy, a phosphonyl, a sulfonyl, a carbonyl, a boronyl, an aryl, a heteroaryl, or [L-TAG]$_n$ wherein $R_1/R_2$, $R_2/R_7$, or $R_4/R_7$ may optionally combine to form a 3-10 member ring; $R_7$ and $R_8$ are independently H, an alkyl, an alkenyl, an alkynyl, an alkoxy, an aryloxy, an alkylthiol, an arylthiol, an aryl, a heteroaryl or [L-TAG]$_n$ wherein $R_7/R_8$ may combine to form a 3-10 member non-aromatic ring; $R_9$ is an aryl, a heteroaryl or [L-TAG]$_n$ wherein $R_7/R_9$ or $R_8/R_9$ may optionally combine to form a 3-10 member non-aromatic ring; X is hydrogen, a counter cation or a moiety that can be cleaved by an enzyme, an ion, light, base or acid; L is a linker; TAG is a biologically detectable moiety; n is an integer from 1 to 100 (e.g., from 1 to 5).

In one aspect of the invention, the compounds of Formula 3 may be used for biological detections in combination with a peroxidase conjugate and a peroxide compound.

Formula 3

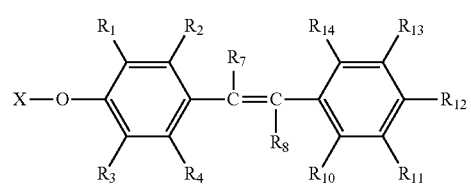

In this embodiment, $R_1$-$R_4$ and $R_{10}$-$R_{14}$ are independently H, an alkyl, a halogen, carboxy, an alkoxy, an aryloxy, thiol, an alkylthiol, an arylthiol, azido, nitro, nitroso, cyano, an amino, hydroxy, a phosphonyl, a sulfonyl, a carbonyl, a boronyl, an aryl, a heteroaryl or [L-TAG]$_n$ wherein $R_1/R_2$, $R_2/R_7$, $R_4/R_7$, $R_7/R_{10}$, $R_7/R_{14}$, $R_8/R_{10}$, $R_8/R_{14}$, $R_{10}/R_{11}$, $R_{11}/R_{12}$, $R_{12}/R_{13}$, or $R_{13}/R_{14}$ may optionally form a 3-10 member ring; $R_7$ and $R_8$ are independently H, an alkyl, an alkenyl, an alkynyl, an alkoxy, an aryloxy, an alkylthiol, an arylthiol, an aryl, a heteroaryl or [L-TAG]$_n$ wherein $R_7/R_8$ may optionally form a non-aromatic 3-10 member ring; X is hydrogen, a counter cation or a moiety that can be cleaved by an enzyme, an ion, light, base or acid; L is a linker; TAG is a dye, a biotin, FITC, DNP, DIG, a luminol, an acridinium ester, a ruthenium complex, an europium complex, a terbium complex, a fluorescent protein, a fluorescent conjugated polymer, or a quantum dot; n is an integer from 1 to 100 (e.g., from 1 to 5).

In one aspect of the invention, the compounds of Formula 4 may be used for biological detections in combination with a peroxidase conjugate and a peroxide compound.

Formula 4

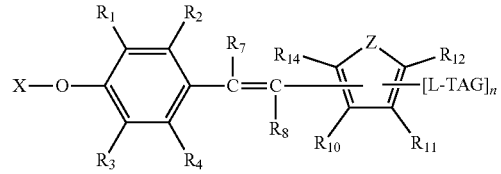

In this embodiment, $R_1$-$R_4$ and $R_{10}$-$R_{14}$ are independently H, an alkyl, a halogen, carboxy, an alkoxy, an aryloxy, thiol, an alkylthiol, an arylthiol, azido, nitro, nitroso, cyano, an amino, hydroxy, a phosphonyl, a sulfonyl, a carbonyl, a boronyl, an aryl or a heteroaryl wherein $R_1/R_2$, $R_2/R_7$, $R_4/R_7$, $R_7/R_{10}$, $R_7/R_{14}$, $R_8/R_{10}$, $R_8/R_{14}$, $R_{10}/R_{11}$, $R_{11}/R_{12}$, or $R_{10}/R_{14}$ may optionally form a 3-10 member ring; $R_7$ and $R_8$ are independently H, an alkyl, an alkenyl, an alkynyl, an alkoxy, an aryloxy, an alkylthiol, an arylthiol, an aryl or a heteroaryl wherein $R_7/R_8$ may optionally form a non-aromatic 3-10 member ring; X is hydrogen, a counter cation or a moiety that can be cleaved by an enzyme, an ion, light, base or acid; L is a linker to connect TAG moiety to the $R_1$ to $R_{14}$ positions; TAG is a dye, a biotin, FITC, DNP, DIG, a luminol, an acridinium ester, a ruthenium complex, an europium complex, a terbium complex, a fluorescent protein, a fluorescent conjugated polymer, a quantum dot, or a radioactive isotope; Z is O, S, $NR_{15}$, or $C(R_{16})$=$NR_{15}$ wherein $R_{15}$ and $R_{16}$ are independently hydrogen, an alkyl, an alkenyl, an alkynyl, an aryl, or an heteroaryl; n is an integer from 1 to 100 (e.g., from 1 to 5).

In one aspect of the invention, the compounds of Formula 5 may be used for biological detections in combination with a peroxidase conjugate and a peroxide compound.

Formula 5

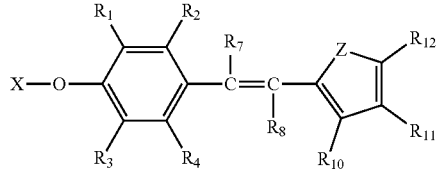

In this embodiment, $R_1$-$R_4$ and $R_{10}$-$R_{12}$ are independently H, an alkyl, a halogen, carboxy, an alkoxy, an aryloxy, thiol, an alkylthiol, an arylthiol, azido, nitro, nitroso, cyano, an amino, hydroxy, a phosphonyl, a sulfonyl, a carbonyl, a boronyl, an aryl, a heteroaryl or [L-TAG]$_n$ wherein $R_1/R_2$, $R_2/R_7$, $R_4/R_7$, $R_7/R_{10}$, $R_7/R_{14}$, $R_8/R_{10}$, $R_8/R_{14}$, $R_{10}/R_{11}$, $R_{11}/R_{12}$, or $R_{10}/R_{14}$ may optionally form a 3-10 member ring; $R_7$ and $R_8$ are independently H, an alkyl, an alkenyl, an alkynyl, an alkoxy, an aryloxy, an alkylthiol, an arylthiol, an aryl, a heteroaryl or $[L-TAG]_n$ wherein $R_7/R_8$ may optionally form a non-aromatic 3-10 member ring; X is hydrogen, a counter cation or a moiety that can be cleaved by an enzyme, an ion, light, base or acid; L is a linker; TAG is a dye, a biotin, FITC, DNP, DIG, a luminol, an acridinium ester, a ruthenium complex, an europium complex, a terbium complex, a fluorescent protein, a fluorescent conjugated polymer, a quantum dot, or a radioactive isotope; Z is O, S, $NR_{15}$, or $C(R_{16})=NR_{15}$ wherein $R_{15}$ and $R_{16}$ are independently hydrogen, an alkyl, an alkenyl, an alkynyl, an aryl, or an heteroaryl; n is an integer from 1 to 100 (e.g., from 1 to 5).

In one aspect of the invention, the compounds of Formula 6 may be used for biological detections in combination with a peroxidase conjugate and a peroxide compound.

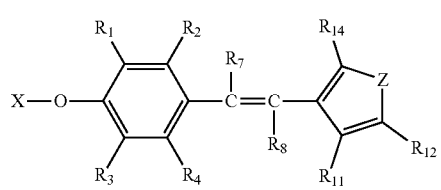

Formula 6

In this embodiment, $R_1$-$R_4$ and $R_1$, $R_{12}$ and $R_{14}$ are independently H, an alkyl, a halogen, carboxy, an alkoxy, an aryloxy, thiol, an alkylthiol, an arylthiol, azido, nitro, nitroso, cyano, an amino, hydroxy, a phosphonyl, a sulfonyl, a carbonyl, a boronyl, an aryl, a heteroaryl or $[L-TAG]_n$ wherein $R_1/R_2$, $R_2/R_7$, $R_4/R_7$, $R_7/R_{10}$, $R_7/R_{14}$, $R_8/R_{10}$, $R_8/R_{14}$, $R_{10}/R_1$, $R_{11}/R_{12}$, or $R_{10}/R_{14}$ may optionally form a 3-10 member ring; $R_7$ and $R_8$ are independently H, an alkyl, an alkenyl, an alkynyl, an alkoxy, an aryloxy, an alkylthiol, an arylthiol, an aryl, a heteroaryl or [L-TAG] wherein $R_7/R_8$ may optionally form a non-aromatic 3-10 member ring; X is hydrogen, a counter cation or a moiety that can be cleaved by an enzyme, an ion, light, base or acid; L is a linker; TAG is a dye, a biotin, FITC, DNP, DIG, a luminol, an acridinium ester, a ruthenium complex, an europium complex, a terbium complex, a fluorescent protein, a fluorescent conjugated polymer, a quantum dot, or a radioactive isotope; Z is O, S, $NR_{15}$, or $C(R_{16})=NR_5$ wherein $R_{15}$ and $R_{16}$ are independently hydrogen, an alkyl, an alkenyl, an alkynyl, an aryl, or an heteroaryl; n is an integer from 1 to 100 (e.g., from 1 to 5).

Detection of a biological or chemical target in a sample using a peroxidase-conjugate is at the heart of many biological detection methods, including medical diagnostic methods. In some cases, the target may be a particular polynucleotide sequence or gene, a mutation of a gene, a genetic expression pattern, detected at the DNA or RNA level, either in situ or after extraction or isolation. In other cases, the target may be a peptide, protein, antigen, or other substance, again detected in situ or after isolation or laboratory manipulation. The target may also be a particle or debris of organic origin.

Many standard detection methods, e.g., IHC, ISH, ELISA, blotting, employ peroxidase labeling schemes to detect the desired targets. Typically, those schemes involve incubating an experimental sample potentially containing a detectable target with a probe, and then detecting the binding between binding agent and target with a detectable label which may give off a color, a fluorescent signal, or radioactivity. One or many binding agent molecules may bind to each target, depending upon the specifics of the scheme used. In some cases, especially when the target is present in low concentration, it is necessary to amplify the signal from the target-binding agent complex by adding one or more amplification layers to the system. For example, if the binding agent is a primary antibody that recognizes the target, a secondary antibody that recognizes the primary antibody may be added such that many secondary antibodies bind to each primary antibody. If the secondary antibodies are attached to a detectable label such as a fluorophore or chromophore, then, via amplification, each target molecule in the sample may effectively be bound to multiple fluorophores or chromophores instead of only one or a few fluorophores or chromophores. Hence, the target will produce a stronger detection signal after amplification.

Some detection experiments, however, have a tendency to produce relatively diffuse-looking signals, especially if the sample is allowed to rest for a period of time before analysis. For example, the one or more binding agents and/or detectable labels bound to a target may slowly diffuse away from the target, or away from each other over time. In some cases, buffer changes that affect the binding affinity of the target, binding agent, and amplification layers can also cause signal diffusion. Many detectable labels are bound to targets by non-covalent interactions such as protein-ligand binding or polynucleotide hybridization. Buffer changes after labeling may reduce the affinity between the target, binding agent, and detectable label, causing the various components to dissociate. The method of this invention provides a greatly improved solution to solve this diffusion problem that is common with many existing biological detection systems.

Anther problem associated with currently available detection procedures, in particular imnnunodetection, is time consumption. It normally takes 1 to 3 hours at minimum to process a sample from the step of labeling of targets to detection of the label. The compositions and methods of this invention may be used in many assay formats, where the target to be detected is a receptor immobilized on a solid support, e.g., a membrane, cell surface, in cells or in tissues. Such assay formats include sandwich immunoassays and membrane-based nucleic acid hybridization assays. Upon reaction with a peroxidase conjugate and a peroxide, a peroxidase substrate of Formula 4 becomes activated and binds to receptor sites of the sample which are typically represented by low abundance aromatic amino acid residues of proteins.

The compositions and methods of this invention allow detection of low abundance target molecules in IHC samples. The deposits of the peroxidase substrate of Formulas 1-6 can be rapidly detected in steps following the deposition step. The compositions and methods of this invention provide a strong amplification of a signal of the deposited peroxidase substrate, which increases the detection sensitivity of the invention. Furthermore, the speed of this detection procedure is much faster than the traditional AEC or tyramide-amplified detection procedures.

The present invention relates to methods and compositions that improve detection of molecular targets. In particular, the methods of the invention allow faster, more sensitive and precise detection of molecular targets than the existing compositions and methods. In one aspect the present invention relates to a method for detecting targets, such as molecular targets or immunological targets. In particular, the invention relates to a method of detecting a target in a sample, comprising:

(i) incubating a target or a sample comprising one or more binding agents comprising a peroxidase conjugate, wherein the one or more binding agents is/are capable of direct or indirect binding to the target, forming a complex comprising the target and one or more binding agents, wherein at least one binding agent comprises peroxidase activity;

(ii) incubating the complex of (i) with a peroxide compound and a compound of Formulas 1-6, wherein the compound has two or more moieties capable of serving as a detectable substrate for a peroxidase enzyme or a peroxidase conjugate to provide a deposited compound;

(iii) detecting the deposited compound, and thereby detecting the target.

In one embodiment a target which may be detected by the method is a polypeptide, nucleic acid, carbohydrate, lipid or a derivative thereof, molecular complex, particle, eukaryotic or prokaryotic cell or microorganism. In one embodiment, a sample may be a biological sample, environmental sample or chemical sample. In one embodiment, a target or sample may be immobilized onto a solid support.

In one embodiment, at least one of the binding agents may be a member of a specific binding pair. In one embodiment the peroxidase activity may be associated with one or more moieties of a peroxidase enzyme bound to one or more binding agents. A preferred peroxidase enzyme of the invention is HRP.

In one embodiment, the detection of the deposited compounds may comprise a step of an enzyme-linked immunodetection. The method, in one embodiment, is for immunohistochemical detection of a target. The method may be performed manually, using automation or semi-automatically. The method of the invention can be successfully plasticized with a number of different reporter molecules described herein, retaining its advantageous features such as a speed of detection, sensitivity and specificity.

In one aspect, the invention relates to a method of detecting target in a sample, e.g., a biological marker, wherein the target is immobilized onto a solid support. In another aspect, it relates to the method where a sample comprising said target is immobilized onto a solid support. The method comprises the step of peroxidase-directed deposition of a reporter molecule of the invention.

In certain embodiments the primary antibody contains an antigen binding region which can specifically bind to a biological marker expressed by cells comprising a biological sample. The marker may be expressed on the cell surface or within the cell membrane, for instance on the interior of the cell, within the cytoplasm, within the nucleus, or within the endoplasmic reticulum. In some embodiments the biological marker is secreted from the cell and accordingly present in solution, e.g., in cell culture media, in blood or plasma.

In certain embodiments, the secondary antibody contains an antigen binding region which specifically binds to the primary antibody, e.g., the constant region of the primary antibody. In certain embodiments, the secondary antibody is conjugated to a polymer. In some embodiments, the polymer is conjugated with 2-20 secondary antibodies, such as 5-15 secondary antibodies. In other embodiments, the polymer is conjugated with 1-10 secondary antibodies, such as 2, 3, 4, 5, 6, 7, 8, or 9 secondary antibodies.

In certain embodiments, the tertiary antibody contains an antigen binding region which specifically binds to the secondary antibody, e.g., a constant region of the secondary antibody, or a hapten linked to the secondary antibody or a polymer conjugated to the secondary antibody. In certain embodiments, the tertiary antibody is conjugated to a polymer. In some embodiments, the polymer is conjugated with 1-20 tertiary antibodies. In other embodiments, the polymer is conjugated with 1-5 tertiary antibodies, such as 2, 3, or 4 tertiary antibodies.

Antibodies used in the methods and compositions of the invention include, without limitation, monoclonal and polyclonal antibodies, engineered antibodies including chimeric, CDR-grafted and artificially selected antibodies produced using phage display or alternative techniques.

Various techniques for producing antibodies have been described (e.g., Kohler and Milstein, Nature, 1975, 256, 495; Harlow and Lane, Antibodies: a Laboratory Manual, 1988, Cold Spring Harbor Press, Cold Spring Harbor, N.Y.). Antibodies may be produced recombinantly or synthetically. Nucleic acids encoding antibodies may be isolated from a cDNA library. Nucleic acids encoding antibodies may be isolated from a phage library (e.g. McCafferty et al. *Nature* 1990, 348, 552; Kang et al. *Proc. Natl. Acad. Sci. USA* 1991, 88, 4363; EP 0589877). Nucleic acids encoding antibodies can be obtained by gene shuffling of known sequences (Mark et al. *Bio/Technol.* 1992, 10, 779). Nucleic acids encoding antibodies can be isolated by in vivo recombination (Waterhouse et al. *Nucl. Acid Res.* 1993, 21, 2265). The antibodies used in the methods and compositions of the invention include humanized immunoglobulins (U.S. Pat. No. 5,585,089; Jones et al. *Nature* 1986, 332, 323). The antibodies may be altered antibodies, for instance, an antibody comprising an effector protein such as a toxin or a label, e.g., a detectable substance.

In one embodiment of the invention, the antibody is represented by the Fab region of an antibody. In another embodiment, the binding agents may be members of a non-immune specific binding pair, such as a complementary nucleotide sequence pair, or a pair of two nucleic acid analog molecules having mutual affinity. A binding agent comprising a nucleic acid or nucleic acid analog molecule, e.g., a DNA molecule, an RNA molecule, a PNA molecule, may be useful for example for detection of nucleic acid targets.

Nucleic acid sequences may be synthesized chemically or produced recombinantly in cells (e.g., Sambrook et al. *Molecular Cloning: A Laboratory Manual*, 1989, Cold Spring Harbor Press). In some embodiments, the binding agent is comprised of a peptide nucleic acid (PNA). A peptide nucleic acid is a nucleic acid molecule in which the deoxyribose or ribose sugar backbone, usually present in DNA and RNA is replaced with a peptide backbone. Methods of making PNAs are known in the art (see e.g., Nielson, *Current Opinion in Biotechnology* 2001, 12, 16). In other embodiments, the binding agent is comprised of locked nucleic acids (LNA) (Sorenson et al., *Chem. Commun.* 2003, 7, 2130).

The binding agent, in some embodiments, may comprise at least one sequence that specifically hybridizes to a target sequence in a biological sample, e.g. a nucleic acid sequence such as a genomic DNA sequence or an mRNA sequence, under specific conditions of stringency. As used herein, the term "hybridization under stringent conditions," is intended to describe conditions for hybridization and washes under which nucleotide sequences that are significantly complementary to each other remain bound to each other. The conditions are such that sequences at least 70%, at least 80%, at least 85-90% complementary remain bound to each other.

Specified conditions of stringency are known in the art (e.g., F. M. Ausubel et al. *Current Protocols in Molecular Biology*, John Wiley & Sons, 1995; M. R. Green and J.

Sambrook, *Molecular Cloning: A Laboratory Manual*, 2001, Cold Spring Harbor Press). In some embodiments, the hybridization conditions are high stringency conditions. It will be understood that additional reagents may be added to hybridization and/or wash buffers, e.g., blocking agents (BSA or salmon sperm DNA), detergents (SDS), chelating agents (EDTA), Ficoll, PVP, etc. In some embodiments, the binding agents may hybridize to a target sequence in a sample under moderately stringent conditions. Moderate stringency, as used herein, include conditions that can be readily determined by those having ordinary skill in the art based on, for example, the length of the DNA.

Some embodiments of the invention may relate to binding agents that may include peptide sequences, e.g. peptide sequences derived from different proteins, e.g., nucleic acid binding domains of different proteins, fragments of ligands of different cellular and nuclear receptors and their derivatives. Some examples of such binding agents may be clq protein of the classical pathway of the complement cascade which can bind to an antibody constant region, a MHC molecule, e.g., MHC class I and MHC class II and non-conventional MHC, a molecule having a specific binding partner, such as molecules involved in cellular signaling pathways such as molecules having leucine zipper domains, e.g., fos/jun, myc, GCN4, molecules having SH1 or SH2 domains, such as Src or Grb-2; an immunoglobulin receptor, e.g., an Fc receptor; a chimeric protein, i.e., a protein engineered to combine the features of two or more specific binding partners, e.g., a leucine zipper could be engineered into a Fc region of an antibody, an SH2 domain could be engineered to be expressed in a Fc region of an antibody. In other embodiments, fusion proteins can be engineered comprising the Fc portion of an antibody with a substituted variable domain. However, this is just a list of non-limiting examples of substances that can be used as binding agents for the purposes of the present invention. The binding agent may also be small molecules which can bind specifically to certain structural units of large biological molecules.

In one embodiment the binding agent is represented by an antibody derivative, preferably the antigen binding domain Fab. The binding agents that are represented by the Fab regions of primary and/or secondary antibodies conjugated with at least one moiety of HRP may be preferred before the corresponding whole antibody binding agents. Such binding agents are more compact molecules than the whole antibody binding agents, and this is advantageous for obtaining a more condensed deposition of a reporter in the proximity to the target site. This may be beneficial for precision detection of the target. This may be of particular advantage when the method of the invention is used for immunohistochemical detection of target molecules, structures or particles in biological samples comprising cells. Immunostaining of target molecules in such samples is especially crisp when the binding agents used are Fab molecules conjugated with a moiety of HRP or they comprise a Fab region and HRP.

Another advantage of using HRP conjugated Fab binding agents is that these binding agents are relatively small in size and therefore have better assess to hidden or masked targets in biological samples that are typically difficult to access when larger antibody-based binding agents are used.

The amount of binding agent used for the detection of a target in an assay using the method of the invention may be significantly reduced compared to the amounts routinely used in the methods of prior art, such as e.g. 100-1000 times reduced, as the invention provides for a strong amplification of a detectable signal associated with the target. The amount of an antibody used for detection of a target in a sample is very much dependent on the antibody, target, or sample. Therefore, this amount should be individually defined in every particular case, which is a routine procedure known to those skilled in the art. When defined, however, the amount of the antibody used for detection of a target by the present method may be up to 1000 times compared to the amount which would be required by most current immunodetection procedures. Possibility of multiple amplification of a signal associated with the target, i.e., first in step of deposition of a reporter of the invention, and then in step of labeling the deposited reporter, makes the detection by the present method also less dependent on the affinity of a primary binding agent, i.e., affinity to the target, because even a weak binding of the binding agent to a target may be detected.

Amplification of a specific signal, i.e., target associated, may be further increased by repeating the deposition step and increasing the amount of deposited reporter in target sites. For example, a reporter deposited in step (ii) of method of the invention may comprises a detectable label that can be specifically recognized by a binding agent comprising peroxidase activity; this sample may be incubated again in a deposition media comprising the same or another reporter molecule, increasing thus the site associated deposit. Notably, in this way, up to 50 rounds of the same target sites directed reporter deposition may be performed without any noticeable non-specific deposition, e.g. in the areas of the sample or solid support with no non-target sites. As mentioned, the reporter molecule to be deposited on the second and further rounds of deposition may be the same reporter, i.e., as used on the first round, or it may be a different reporter molecule. The second or further reporter molecules may be molecules that produce more robust signal or comprise an increased amount of detectable labels; in this way the target site associated signal may be alternatively or/and further enhanced.

Accordingly, the method also provides for flexibility of the detection procedure, and for reproducible detection of targets in a huge variety of samples immobilized onto a solid support. The method is very advantageous for immunochemical detection of targets in challenging samples such as histological samples, as it provides for a very crisp and specific immunochemical labeling of molecular targets and thus facilitates interpretation and quantification of the sample content.

In one embodiment, the peroxidase activity may be represented by a molecule of a peroxidase enzyme which is directly or indirectly linked to the molecule of a binding agent, or a fragment of the enzyme conflated with the enzymatic activity, e.g., 51% to 99.9% of the full size of the peroxidase molecule, or less than 51%. A binding agent of the invention may be directly or indirectly conjugated with one or more peroxidase moieties. Molecules of both or either first and/or second binging agents may be conjugated with one or several functionally active moieties of a peroxidase. In one embodiment at least one molecule of a first binding agent may be conjugated with one or more peroxidase moieties; in another embodiment at least. one molecule of a second binding agent may be conjugated with one or more peroxidase moieties. Molecules of third and further binding agents may also be conjugated with a peroxidase. The term "directly conjugated" means that the enzyme moiety is linked to the molecule of a binding agent via a chemical bond. The term "indirectly conjugated" means that the peroxidase is linked to the molecule of a binding agent via a linking molecule, which has one chemical bond with binding agent and another chemical bond with peroxidase. Embodiments of linking molecules are discussed below.

In one embodiment the moiety of peroxidase is a moiety of HRP, e.g., the whole HRP molecule a fragment that is capable of the HRP enzymatic activity, it may also be a recombinant protein comprising the part of HRP that possesses the enzymatic activity, etc. In another embodiment the peroxidase may be soybean peroxidase.

Non-limiting examples of binding agents which comprise an enzyme with peroxidase activity may be a primary or secondary antibody molecule or a derivative thereof, e.g., a Fab, conjugated with one or more moieties of the full-length HRP, and nucleic acid binding agents conjugated with HRP. Such binding agents may bind directly or indirectly to the target molecules and form thereby complexes each comprising one or more molecules of binding agents that comprise an enzyme with peroxidase activity.

In one embodiment the binding agent is a conjugate comprising one, or two or more peroxidase moieties that are directly linked to the binding agent, e.g. an antibody molecule linked to one or more HRP moieties. In another embodiment the binding agent is a conjugate that comprises two or more functional moieties of a peroxidase that are linked to the binding agent indirectly, such as a conjugate wherein one or more molecules of an antibody and one or more HRP moieties independently linked to a backbone polymer (a binding agent wherein the enzyme with peroxidase activity is indirectly linked to the binding agent, the antibody). The number of HRP per molecule of binding agent may vary from 1 to 10 or be even higher, e.g. 20-50 or be even higher.

In some embodiments, small conjugate molecules of binding agents, e.g., single antibody molecules or their Fab regions that are conjugated with one, or two, or more moieties of a peroxidase, such as HRP, may be preferred. Such binding agents are relatively compact molecules, and this feature may be advantageous for detecting hidden targets, e.g. target molecules, structures or particles in complicated biological samples comprising cells. In other embodiments, large conjugates comprising a binding agent and tens to hundreds enzyme moieties may be preferred. Such binding agents may be advantageous, for example, in cases where very fast target detection is concerned or obtaining large deposits per individual target site are desirable.

A site of a solid support comprising peroxidase activity is termed herein "target site". In one embodiment the target site comprises peroxidase activity, such as a moiety of a peroxidase enzyme, which is directly immobilized onto or within a solid support. In another embodiment the target site comprises peroxidase activity which is immobilized onto or within a solid support indirectly, i.e., a moiety of a peroxidase enzyme is linked to a binding agent capable of directly or indirectly binding to a target that is immobilized onto or within a solid support. The latter are non-limiting examples of the target site of the invention.

The method of the invention may be performed in a great variety of assay formats. Target molecules comprising cells of a cell suspension may be detected employing the compositions and methods described above in any suitable assay format, for example in flow cytometry (FC), or ELISA, or immunohytochemistry (IHC), or in situ hybridization (ISH). In one embodiment the biological sample may be a suspension of cells. Target molecules or structures of cells in suspension may be detected using FC, ELISA, IHC or ISH. When ELISA, IHC or ISH are used for detection, cells of the suspension are to be attached to a solid support, e.g. ELISA plate or ICH slide. In another embodiment the biological sample may be a slice of a body tissue. Target molecules or structures of cells of such samples will be typically detected using IHC or ISH.

IHC and ISH assay formats usually require a series of treatment steps conducted on a tissue section mounted on a suitable solid support for microscopic inspection, or the production of photomicrographs, e.g., a glass slide or other planar support, to highlight by selective staining certain morphological indicators of disease states or detection of biological markers. Thus, for example in IHC, a sample is taken from an individual, fixed and exposed to antibodies which specifically bind to the biological marker of interest. The sample processing steps may include, for example, antigen retrieval, exposure to a primary antibody, washing, exposure to a secondary antibody (optionally coupled to a HRP moiety), washing, and exposure to a tertiary antibody linked to one or more HRP moieties. Washing steps may be performed with any suitable buffer or solvent, for instance, phosphate-buffered saline (PBS), tris buffered saline (TBS), distilled water. The wash buffer may optionally contain a detergent such as Tween 20.

Histological samples may be the preparations comprising fresh tissues and/or cells, which generally are not fixed with aldehyde-based fixatives, or fixed and embedded tissue specimens, often archived material. Before performing detection of a target in the IHC assay format, a pre-detection procedure is to be performed. It may involve the steps of: cutting and trimming tissue, fixation, dehydration, paraffin infiltration, cutting in thin sections, mounting onto glass slides, baking, deparaffination, rehydration, antigen retrieval, blocking steps, applying primary antibody, washing, applying secondary antibody-enzyme conjugate and washing.

In ISH, a sample is taken from an individual, fixed and exposed to a nucleic acid binding agent which hybridizes by virtue of complementary base pairing to the nucleic acid of interest. The biological sample typically comprises a detectable nucleic acid, such as DNA and RNA, including messenger RNA. Detection of DNA/RNA levels may indicate the level of expression of a particular gene, and hence may be used to detect a condition (such as a disease condition) of a cell, tissue, organ or organism. The nucleic acid in the sample is typically denatured to expose binding sites. The binding agent is typically a double or single stranded nucleic acid, such as a DNA or RNA, or a nucleic acid analog, such as PNA. The amount of the relevant target protein or nucleic acid detected by such techniques is then assessed to determine whether it is above a certain pre-determined minimum threshold or compared to a known standard, and therefore, diagnostically relevant. Suitable treatment may then be planned for the individual if necessary.

Many methods of fixing and embedding tissue specimens are known, for example, alcohol fixation and formalin-fixation and subsequent paraffin embedding (FFPE). Fixatives are needed to preserve cells and tissues in a reproducible and life-like manner. To achieve this, tissue blocks, sections, or smears are immersed in a fixative fluid, or in the case of smears, are dried. Fixatives stabilize cells and tissues thereby protecting them from the rigors of processing and staining techniques.

Any suitable fixing agent may be used, for example, ethanol, acetic acid, picric acid, 2-propanol, 3,3'-diaminobenzidine tetrahydrochloride dihydrate, acetoin (mixture of monomer) and dimer, acrolein, crotonaldehyde, formaldehyde, glutaraldehyde, glyoxal, potassium dichromate, potassium permanganate, osmium tetroxide, paraformaldehyde, mercuric chloride, tolylene-2,4-diisocyanate, trichloroacetic acid, tungstic acid. Other examples include formalin (aqueous formaldehyde) and neutral buffered formalin (NBF), glutaraldehyde, acrolein, carbodiimide, imidates, benzoequinone, osmic acid and osmium tetraoxide.

Fresh biopsy specimens, cytological preparations (including touch preparations and blood smears), frozen sections and tissues for immunohistochemical analysis are commonly fixed in organic solvents, including ethanol, acetic acid, methanol and/or acetone.

To facilitate the specific recognition in fixed tissue, it is often necessary to retrieve or unmask the targets, i.e., the biological markers of interest, through pre-treatment of the specimens to increase reactivity of the majority of targets. This procedure is referred to as "antigen retrieval", "target retrieval" or "epitope retrieval", "target unmasking" or "antigen unmasking" (e.g., S. R. Shi et al. *J Histochem Cytochem,* 1997, 45, 327). Antigen retrieval includes a variety of methods by which the availability of the target for interaction with a specific detection reagent is maximized. The most common techniques are enzymatic digestion with a proteolytic enzyme (for example proteinase, pronase, pepsin, papain, trypsin or neuraminidase) in an appropriate buffer or heat induced epitope retrieval (HIER) using microwave irradiation, heating in a water bath, a steamer, a regular oven, an autoclave or a pressure cooker in an appropriately pH stabilized buffer, usually containing EDTA, EGTA, Tris-HCl, citrate, urea, glycine-HCl or boric acid. Detergents may be added to the HIER buffer to increase the epitope retrieval or added to the dilution media and/or rinsing buffers to lower non-specific binding. The antigen retrieval buffer is most often aqueous, but may also contain other solvents, including solvents with a boiling point above that of water. This allows for treatment of the tissue at more than 100° C. at normal pressure. Additionally, the signal-to-noise ratio may be increased by different physical methods, including application of vacuum and ultrasound, or freezing and thawing of the sections before or during incubation of the reagents.

Endogenous biotin binding sites or endogenous enzyme activity (for example phosphatase, catalase or peroxidase) may be removed as a step in the detection procedure, e.g., endogenous biotin and peroxidase activity may be removed by treatment with peroxides. Endogenous phosphatase activity may be removed by treatment with levamisole. Endogenous phosphatases and esterases may be destroyed by heating. Blocking of non-specific binding sites with inert proteins like, horse serum albumin (HSA), casein, bovine serum albumin (BSA), and ovalbumin, fetal calf serum or other sera, or detergents like Tween20, Triton X-100, Saponin, Brij or Pluronics may be used. Blocking non-specific binding sites in the tissue or cells with unlabeled and target non-specific versions of the specific reagents may also be used.

Samples may also be prepared, and target molecules detected using the free floating technique. In this method a tissue section is brought into contact with different reagents and wash buffers in suspension or freely floating in appropriate containers, for example micro centrifuge tubes.

The tissue sections may be transferred from tube to tube with different reagents and buffers during the staining procedure using for example a "fishing hook like" device, a spatula or a glass ring. The different reagents and buffer can also be changed by gentle decantation or vacuum suction. Alternatively, containers with the tissue sections can be emptied into a special staining net, and the tissue section washed before being transferred back into the tube for the next staining step.

All the steps, including for example fixation, antigen retrieval, washing, incubation with blocking reagents, immuno-specific reagents and the peroxidase-mediated reporter deposition, are done while the tissue section is floating freely or withheld on nets. After deposition of the reporter, the tissue section is mounted on slides, the reporter is detected, and slide covered with a cover slip before being analyzed, e.g., by light or fluorescence microscopy.

In some embodiments, the tissue section may be mounted on slides following the critical incubation with the immuno-specific reagents following the procedure (a) of the method. The rest of the process of detection is then conducted on the slide mounted tissue sections.

The biological marker may be any molecule or structure present in a sample that is detectable by the method, preferably in a biological sample, e.g., a protein, glycoprotein, lipoprotein, phosphoprotein, methylated protein, or a protein fragment, e.g., a peptide or a nucleic acid, e.g., DNA, RNA, a lipid, a glycolipid, or a sugar, a polysaccharide, or a starch. The biological marker may be expressed on the surface of the biological sample, for example, membrane bound. The marker may be contained in the interior of the biological sample, such as within the cell membrane, e.g., within the cytoplasm, within the nucleus, within an intracellular compartment or organelle. The biological marker may be a cellular structure, such as a membrane microdomain, ion channel, chromosomal structure, etc., or it may be a molecular complex, e.g. RNA-protein complex. A biological marker is preferably a specific biological marker, for example it is a marker of a normal or pathological condition, or it is specific for a particular cell or tissue, or specific for a particular biological species. Detection of such biological marker may be useful in diagnosis and treatment of pathological conditions.

The compositions and methods of the invention may be used for detection of one or more targets in a sample, such as one or more biological markers in a biological sample. Accordingly, the invention also provides for obtaining data of diagnostic and therapeutic relevance, including, without limitation, information concerning the presence of protein and gene markers of diagnostic relevance. For example, HER2 protein and the HER2 gene can be screened simultaneously in a cancer diagnostic assay, e.g., an assay for breast cancer. Another non-limiting example may include screening for three markers, e.g., to detect cervical cancer. The markers may include Ki67/mib-1, as well as the cellular proliferation marker, p16(INK4a), along with a marker, e.g., a protein or nucleic acid, for human papilloma virus. Yet another non-limiting example includes screening for multiple markers associated with prostate cancer. These markers may include AMACR P504S, high molecular weight cytokeratin and p63. Screening this combination of markers provides a method to distinguish benign prostate tumors from malignant ones.

It is desirable to minimize cross-reactivity between binding agents, e.g. where multiple markers are detected. This can be accomplished, for example, by using different binding agents and different reporter molecules in the detection procedures. A system where two different biological markers are detected may comprise the following steps:

a) performing steps (i) and (ii) using a first binding agent specific for a first biological marker and first reporter comprising a first detectable label;

b) performing steps (i) and (ii) using a second binding agent specific for a second biological marker and a second reporter comprising a second detectable label;

c) detecting the deposited first reporter and thereby detecting the first biological marker;

d) detecting the deposited second reporter and thereby detecting the second biological marker.

In one embodiment every step of a method of the invention (including every washing step) may be performed the same incubation time, e.g., 30 sec each step, 1 min each step, 2 min each step, 3 min each step, 4 min each step, etc. In another embodiment, time intervals used for performance of each step may vary. All steps of the method (from (i) to (iii) including the washing steps) may be completed within 2-20 min. Such rapid detection may be advantageously used for automated or semi-automated detection of target biological markers. In one embodiment the method is for a manual, automated or semi-automated detection.

Automated staining devices may be used in various embodiments of the invention, for example for the detection of multiple biological markers. Detection of multiple markers frequently requires balancing of the signals derived from the different detectable labels. An automated procedure may include multiple steps of amplification of the signals emanating from target biological markers. It is especially advantageous when multiple markers are to be detected. Automated staining devices are known in the field and the method may be adapted for these devices. The method may be performed within a wide range of temperatures, e.g., in the interval from 4 to 60° C., such as from 10 to 40° C., for example at room temperature.

In certain embodiments, the invention provides for a more sensitive method, compared to known methods, of detecting a biological marker in a sample, e.g., by IHC. Increased sensitivity may provide a stronger detection signal generated from a stained sample. Increased sensitivity may permit the use of less reagents, e.g., a primary antibody, a secondary antibody when performing IHC or other immunologically based detection methods, and less reagent may provide for a reduction in unspecific background staining. Alternatively, the increased sensitivity may be utilized to perform a faster protocol.

In some embodiments, the invention provides a composition useful for detecting a biological marker in a sample comprising a first binding agent which specifically binds to a biological marker in a sample, (e.g., a primary antibody, a nucleic acid probe) a second binding agent which specifically binds to the first binding agent, (e.g. a secondary antibody), and a third binding agent which specifically binds to the second binding agent, (e.g., a tertiary antibody). At least one of the binding agents may be linked to a polymer or the binding agents themselves may be polymerizable, e.g., derivatized and polymerized. The conjugated polymer may be linked with a detectable substance. In some embodiments, at least one of the second binding agent and the third binding agent may be linked to a detectable substance or a hapten or both a detectable substance and a hapten. The invention also provides a method of detecting a biological marker in a sample comprising contacting the sample with the composition of the invention.

In some embodiments, the invention provides a composition comprising at least a primary antibody, a secondary antibody and a tertiary antibody, where at least one of the tertiary antibody and the secondary antibody is linked to a polymer conjugated to a detectable substance or is itself derivatized and then polymerized, optionally with a detectable substance. The composition is useful in detecting biological markers in a sample by IHC. The composition is also useful for detecting markers associated with a disease or condition, e.g., a protein expressed at higher levels in a cell or tissue sample derived from a subject having a disease compared to a cell or a tissue sample derived from a subject not having the disease.

In certain embodiments, the invention provides for a method of detecting a biological marker in a sample comprising a) contacting the sample with at least one primary antibody, chosen from a mouse antibody and a rabbit antibody such that the at least one primary antibody binds to the sample forming a first complex; b) contacting the complex of a) with i) at least one first secondary goat antibody linked to a first dextran polymer, the first secondary goat antibody comprising an antigen binding domain which specifically binds to a mouse antibody; ii) at least one second secondary goat antibody linked to a second dextran polymer, the second secondary goat antibody comprising an antigen binding domain which specifically binds to a rabbit antibody; wherein at least one hapten molecule is linked to at least one of 1) the at least one secondary goat antibody; 2) at least one of the first and second dextran molecule; and 3) the at least one secondary goat antibody and at least one of the first and second dextran molecule such that the at least one secondary antibody binds to the complex of a) forming a second complex; c) contacting the second complex of b) with i) at least one tertiary antibody, chosen from a rabbit antibody, a mouse antibody, a rat antibody, a porcine antibody and a goat antibody, linked to a third dextran polymer, the at least one tertiary antibody comprising an antigen binding domain which specifically reacts with the at least one hapten molecule of b); wherein at least one horse radish peroxidase molecule is linked to at least one of 1) the tertiary antibody; 2) the at least one third polymer; and 3) both the tertiary antibody and the at least one third polymer such that the tertiary antibody binds to the second complex of b) and forms a third complex; and d) detecting the third complex of c).

In one embodiment, the invention provides a composition comprising: a) at least one primary antibody; b) at least one secondary antibody, optionally linked to a first polymer, the at least one secondary antibody comprising an antigen binding domain which specifically binds to the primary antibody; and c) at least one tertiary antibody linked to at least one second polymer wherein a detectable agent is linked to at least one of i) the at least one tertiary antibody; ii) the at least one the second polymer; and iii) both the tertiary antibody and at the least one second polymer.

TABLE 1

Examples of Binding and Bonding Pairs for Indirect Detections

| Tag | Detection Partner |
|---|---|
| Biotin | Avidin/streptavidin/ anti-biotin |
| Dinitrophenyl (DNP) | Anti-DNP |
| TNP | Anti-TNP |
| FLAG | Anti-FLAG |
| HA | Anti-HA |
| Poly-His | NTA-Ni$^{2+}$ |
| Myc | Anti-c-Myc |
| V5 | Anti-V5 |
| S | Anti-S |
| E | Anti-E |
| T7 | Anti-T7 |
| VSV-G | Anti-VSV-G |
| Glu-Glu | Anti-Glu-Glu |
| Strep-tag II | Anti-Strep-tag II/streptavidin |
| HSV | Anti-HSV |
| CBD (Chitin Binding Domain) | Anti-CBD |
| CBP (Calmodulin Binding Peptide) | Anti-CBP |

TABLE 1-continued

Examples of Binding and Bonding Pairs for Indirect Detections

| Tag | Detection Partner |
| --- | --- |
| GST (Glutathione-S-transferase) | Anti-GST |
| MBP (Maltose Binding Protein) | Anti-MBP |
| Thioredoxin | Anti-thioredoxin |
| Digoxigenin (DIG) | Anti-DIG |
| FITC | Anti-FITC |
| Azide | Alkyne/DBCO |
| Tetrazine | TCO |
| Hydroxylamines | Aldehydes/ketones |
| Hydrazines | Aldehydes/ketones |
| Cysteines | Aldehydes/ketones |
| Aryl azides | Methyl 2-diphenylphosphinobenzonate |
| Nitrile-N-oxides | Cycloalkynes |
| Anthracenes | Maleimides |

Applications of the Compositions and Methods of the Invention

The examples provided below illustrate selected aspects of the invention. They are not intended to limit or define the entire scope of the invention.

EXAMPLES

Example 1. Preparation of Compound 100

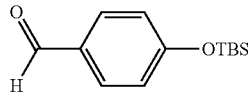

To the solution of 4-hydroxybenzaldehyde (2.70 g, 22.1 mmol) in DMF (30 mL) with Et$_3$N (6.17 mL), TBSCl (5.00 g, 33.2 mmol) is added slowly at 0° C. After 10 minutes stirring at 0° C., the resulting reaction mixture is stirred at room temperature for another 2 hours. After solvent is evaporated, water is added and extracted with DCM. The DCM solution is washed with brine, dried over anhydrous Na$_2$SO$_4$, filtered and concentrated under vacuum. The crude product is purified on a silica gel column chromatography to give Compound 100 as colorless oil.

Example 2. Preparation of Compound 104

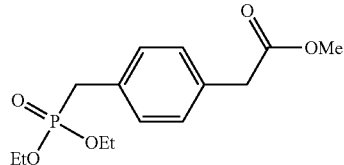 [SMILES: CCOP(=O)(Cc1ccc(CC(=O)OC)cc1)OCC]

The mixture of methyl 2-(4-bromomethylphenyl)acetate (0.71 g) and triethylphophite (6.22 g, 6.5 mL) is heated up to 145° C. for 2 hours. After the reaction is cooled to room temperature, most of the solvent is evaporated and the crude material is purified by silica gel column to give Compound 104.

Example 3. Preparation of Compound 105

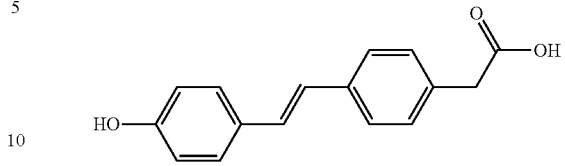

To the DCM solution (15 mL) of compound 104 (0.56 g, 1.88 mmol) and Compound 100 (0.89 g, 3.76 mmol) at 0° C., KOtBu (0.53 g, 4.70 mmol) is added in portion. After stirred at 0° C. for 30 minutes, the reaction mixture is allowed to stir at room temperature for another 1.5 hour. The reaction is quenched with saturated aqueous NaHCO$_3$ solution and extracted with DCM. The DCM layer is washed with brine, dried over anhydrous Na$_2$SO$_4$, filtered and concentrated under vacuum.

The crude is dissolved in THF (10 mL), 1 M TBAF solution in THF (3 mL) is added and stirred at room temperature for 15 mins. To the reaction mixture, 1 M NaOH/H$_2$O solution, MeOH and THF are added to get a clear solution. The resulting mixture is stirred at room temperature for 30 minutes. The organic solvents are evaporated, and then the pH of the residue is adjusted to 8 with 1 M TEAB/H$_2$O solution and purified by C-18 column chromatography. The pure fractions are combined and concentrated to around 10 mL. The pH value of the solution is adjusted to 2 with 1 M HCl/H$_2$O solution, and then extracted with EtOAc. The EtOAc is dried over anhydrous Na$_2$SO$_4$, filtered and concentrated to give Compound 105 as light-yellow solid.

Example 4. Preparation of Compound 106

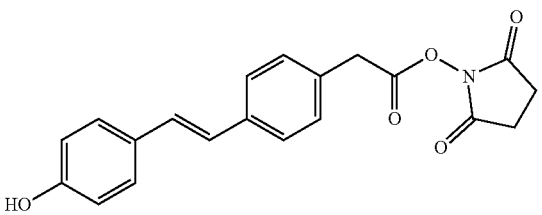 [SMILES: O=C(Cc1ccc(/C=C/c2ccc(O)cc2)cc1)ON1C(=O)CCC1=O]

To a THF solution (3 mL) of compound 105 (37 mg, 0.15 mmol) with pyridine (0.5 mL), N-hydroxysuccinimidyl trifluoroacetate (92 mg, 0.44 mmol) is added in one portion. The resulting mixture is stirred at room temperature for 20 minutes. After evaporation of the solvent, the residue is diluted with EtOAc and washed with 0.3 N HCl/H$_2$O solution, water and brine. The organic layer is dried over Na$_2$SO$_4$, filtered and concentrated under vacuum. The crude is dissolved in EtOAc (1 mL) and a few drops of MeOH, and then precipitated out in hexane (50 mL). The solid is collected through centrifuge and dried under vacuum to give Compound 106 as white solid.

Example 6. Preparation of Compound 110

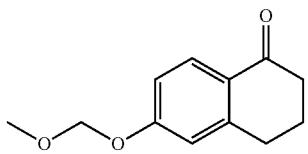

To the mixture of 6-hydroxy-3,4-dihydronaphthalen-1 (2H)-one (3.2 g) and $K_2CO_3$ (11 g) in DMF (20 mL) is added MOMCl (3.3 g). The reaction mixture is stirred at room temperature for 4-8 hours. The reaction is monitored for completion by TLC. The reaction solution is diluted with ethyl acetate (200 mL), and then mixed with water (200 mL). The two layers are separated, and the aqueous phase is extracted with additional ethyl acetate (3×50 mL). The combined organic layers are washed with brine, and then dried over $MgSO_4$. The combined organic solution is concentrated under reduced pressure. The residue is purified on a silica gel column chromatography eluted with a gradient of chloroform/ethyl acetate.

Example 7. Preparation of Compound 114

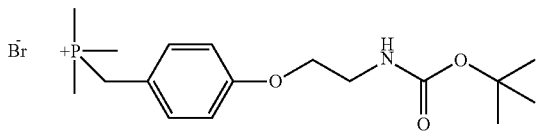 [SMILES: Br ; CC(C)(C)OC(=O)NCCOc1ccc(C[P+](C)(C)C)cc1]

To the solution of tert-butyl (2-(4-(bromomethyl)phenoxy)ethyl)carbamate (3 g, Xian Biolite) in MeCN (100 mL) add triphenylphosphine (3 g). The reaction mixture is refluxed for 24-48 hours. The reaction is monitored for completion by TLC. The reaction solution is cooled to room temperature, and then diluted with ethyl ether (200 mL). The suspension is filtered to collect the solid that is washed with toluene (3×50 mL). The solid is further dried under high vacuum.

Example 8. Preparation of Compound 118

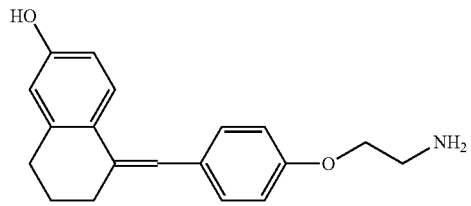 [SMILES: NCCOc1ccc(C=C2CCCc3cc(O)ccc32)cc1]

To the suspension of Compound 114 (4.1 g) in THF (20 mL) is dropwise added n-BuLi (4 mL, 2.5 M in hexane). The mixture is stirred at room temperature for 2 hours. To the THF mixture of Compound 114 is added the solution of Compound 110 (2.3 g) in THF (50 mL). The reaction is stirred at room temperature for a few minutes, and then refluxed until completion as monitored by TLC. The reaction solution is cooled to room temperature, and then quenched with water (200 ml). The water solution is extracted with ethyl acetate (3×100 mL). The combined organic layers are washed with brine, and then dried over $MgSO_4$. The organic solution is concentrated under reduced pressure. The residue is purified on a silica gel column chromatography eluted with a gradient of hexanes/ethyl acetate. The pooled pure fractions are pooled, and then evaporated to give a solid. The solid is dissolved in DCM (200 ml) with the addition of anisole (100 mg). To the solution is dropwise added trifluoracetic acid (1 mL) at room temperature. The solvent is removed in vacuo and the crude material is purified by C18 reverse phase HPLC (water/MeCN with TFA) to provide the desired pure product.

Example 9. Preparation of Compound 120

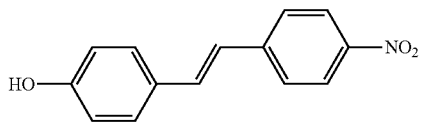 [SMILES: O=[N+]([O-])c1ccc(/C=C/c2ccc(O)cc2)cc1]

To a DMF solution (15 mL) of 4-nitrotoluene (0.69 g, 5 mmol) and Compound 100 (0.89 g, 3.76 mmol) at room temperature, KOH (1.2 g) is added. After stirred at room temperature for 3.0 minutes, the reaction mixture is heated at 120° C. for another 2 hours. The reaction is extracted with DCM. The DCM layer is washed with brine, dried over anhydrous $Na_2SO_4$, filtered and concentrated under vacuum.

The crude is dissolved in THF (10 mL), 1 M TBAF solution in THF (3 mL) is added and stirred at room temperature for 15 mins. To the reaction mixture, 1 M $NaOH/H_2O$ solution, MeOH and THF are added to get a clear solution. The resulting mixture is stirred at room temperature for 30 minutes. The organic solvents are evaporated, and then the pH of the residue is adjusted to 8 with 1 M $TEAB/H_2O$ solution and purified by C-18 column chromatography. The pure fractions are combined and concentrated to around 10 mL. The pH value of the solution is adjusted to 2 with 1 M $HCl/H_2O$ solution, and then extracted with EtOAc. The EtOAc is dried over anhydrous $Na_2SO_4$, filtered and concentrated to give Compound 105 as light yellow solid.

Example 11. Preparation of Compound 121

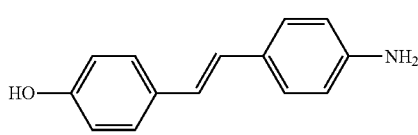 [SMILES: Nc1ccc(/C=C/c2ccc(O)cc2)cc1]

To a MeOH solution (15 mL) of compound 120 (0.48 g, 2 mmol) stannous chloride (0.57 g, 3 mmol) is added in three portions at room temperature. The reaction mixture is refluxed for another 3 hours. The reaction is cooled to room temperature and neutralized with saturated aqueous NaHCO$_3$ solution (pH~3). The reaction mixture is evaporated to remove MeOH. The residual is diluted with water (200 mL) and extracted with EtOAc (2×100 mL). The EtOAc layer is washed with brine, dried over anhydrous Na$_2$SO$_4$, filtered and concentrated under vacuum. The crude residue is purified on a silica gel column to give the pure product using a gradient of CHCl$_3$/MeOH.

Example 10. Preparation of Compound 122

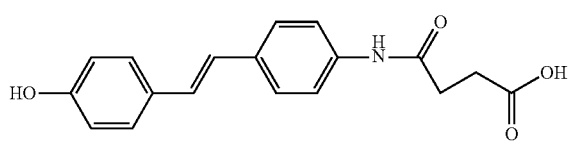 [SMILES: O=C(O)CCC(=O)Nc1ccc(/C=C/c2ccc(O)cc2)cc1]

To a THF solution (30 mL) of compound 121 (0.42 g, 2 mmol) is added succinic anhydride (0.5 g, 5 mmol) in one portion at room temperature, followed by the addition 5 mL pyridine. The reaction mixture is allowed to stir at room temperature for another 6 hours. The mixture is concentrated under high vacuum, and the residue is redissolved in MeOH (50 mL). The MeOH solution is treated 0.1N NaOH (50 mL) with stirring at room temperature for 2 hours. The reaction mixture is concentrated and diluted with water (50 mL). The combined solution is neutralized with concentrated HCl and extracted with EtOAc. The EtOAc layer is washed with brine, dried over anhydrous Na$_2$SO$_4$, filtered and concentrated under vacuum. The crude residue is purified on a silica gel column to give the pure product using a gradient of EtOAc/MeOH.

Example 12. Preparation of Compound 121

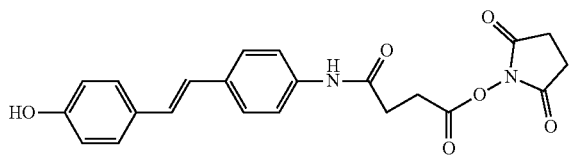 [SMILES: O=C(CCC(=O)ON1C(=O)CCC1=O)Nc1ccc(/C=C/c2ccc(O)cc2)cc1]

To the solution of Compound 120 (350 mg, 0.1 mmol) in DMF (4 mL) is added O—(N-succinimidyl)-N,N,N',N'-tetramethyluronium tetrafluoroborate (35 mg, 0.12 mmol), followed by triethylamine (0.3 mL). The mixture is stirred at room temperature for 1 hour. The solution is poured into EtOEt (15 mL). The solid is centrifuged and washed with EtOEt (3×10 mL), ether (1×10 mL) and dried under vacuum to give Compound 121 as light yellow powder.

Example 13. Preparation of Compound 122

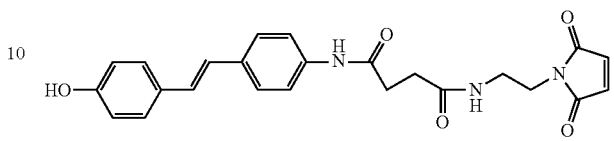

To Compound 121 (100 mg) in DMF (1 mL) at room temperature is added 4 equivalents of triethylamine and 1.2 equivalents of N-(2-aminoethyl)maleimide, trifluoroacetic acid salt (Sigma-Aldrich). The mixture is stirred at ambient temperature for 60 minutes. The DMF solution is poured into ether, and resulted suspension is centrifuged to collect the solid that is air-dried. The crude product is further purified with silica gel chromatography to yield the desired Compound 122.

The compounds of the invention may be prepared using any suitable synthetic schemes. The methodology used to prepare the compounds of the invention may involve two components. The first component may involve the formation of the styryl phenol moieties, while the second may involve the conjugation of a styryl phenol moiety with a TAG such as a dye through a linker. Although these synthetic components are typically performed in the order given, they may be carried out in any other suitable sequences. For example, a portion of the styryl phenol moiety or TAG may be derivatized with a protection group prior to conjugation. The appropriate methods may be used to synthesize the desired compounds of the invention.

The syntheses of styryl compounds have been well summarized in the literature. There are many methods that can be used for preparing styryl intermediates including Peterson Reactions, Wittig Reaction, various Ylids, and phosphonates etc. (e.g., see M. Trost et al., Comprehensive Organic Synthesis, 1991, 1, 729; J. Boutagy et al., Chem Rev, 1974, 74, 87; J. Boutagy et al., Chem Rev, 1989, 89, 863; D. J. Ager, Organic Reactions, 1990, 38, 1). These methods are well-known to the ones skilled in the art and can be readily adapted to prepare the styryl phenols of the inventions as exemplified above with the additional examples as listed in Table 2. Post-condensation modifications of the styryl phenols are typically analogous to the known methods. For example, the reduction of nitro or nitro substituents to amino groups, the conversion of carboxy substituents to cyano groups, and the preparation of esters and amides of carboxylic acids. Additionally, a given salt or counterion of the compounds of the invention may be readily converted to other salts by treatment with ion-exchange resins, selective precipitation, and basification etc.

TABLE 2
Some styryl phenols useful for making the compounds of invention
| Compound Code | Structure |
|---|---|
| 130 | 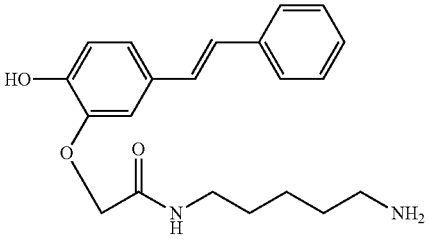 [SMILES: NCCCCCNC(=O)COc1cc(/C=C/c2ccccc2)ccc1O] |
| 131 | 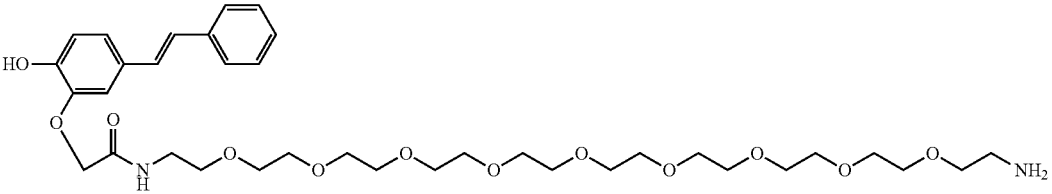 [SMILES: NCCOCCOCCOCCOCCOCCOCCOCCOCCOCCNC(=O)COc1cc(/C=C/c2ccccc2)ccc1O] |
| 132 | 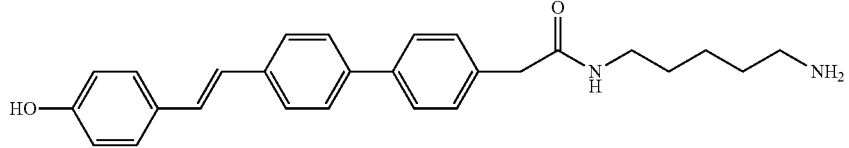 [SMILES: NCCCCCNC(=O)Cc1ccc(-c2ccc(/C=C/c3ccc(O)cc3)cc2)cc1] |
| 133 | 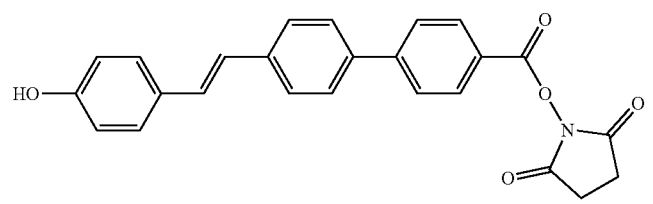 [SMILES: O=C(ON1C(=O)CCC1=O)c1ccc(-c2ccc(/C=C/c3ccc(O)cc3)cc2)cc1] |
| 134 | 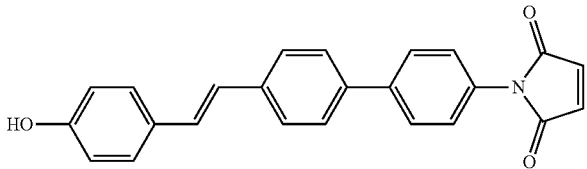 [SMILES: O=C1C=CC(=O)N1c1ccc(-c2ccc(/C=C/c3ccc(O)cc3)cc2)cc1] |
| 135 | 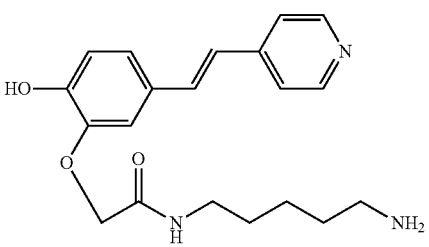 [SMILES: NCCCCCNC(=O)COc1cc(/C=C/c2ccncc2)ccc1O] |
| 136 | 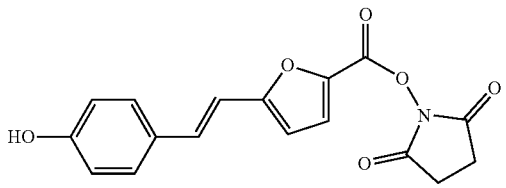 [SMILES: O=C(ON1C(=O)CCC1=O)c1ccc(/C=C/c2ccc(O)cc2)o1] |

TABLE 2-continued

Some styryl phenols useful for making the compounds of invention

| Compound Code | Structure |
|---|---|
| 136 | 4-hydroxystyryl-furan-2-carboxamide-N-(5-aminopentyl) |
| 137 | 4-hydroxystyryl-furan-2-carboxamide-N-(5-(maleimido)pentyl) |
| 138 | 4-hydroxystyryl-thiophene-2-carboxylic acid N-hydroxysuccinimide ester |
| 139 | 4-hydroxystyryl-thiophene-2-carboxamide-N-(5-aminopentyl) |
| 140 | 4-hydroxystyryl-thiophene-2-carboxamide-N-(5-(maleimido)pentyl) |
| 141 | 4-hydroxystyryl-1H-pyrrole-2-carboxylic acid N-hydroxysuccinimide ester |
| 142 | 4-hydroxystyryl-1H-pyrrole-2-carboxamide-N-(5-aminopentyl) |
| 143 | 4-hydroxystyryl-1H-pyrrole-2-carboxamide-N-(5-(maleimido)pentyl) |

TABLE 2-continued
Some styryl phenols useful for making the compounds of invention
| Compound Code | Structure |
|---|---|
| 144 | 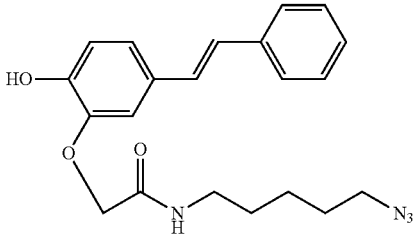 [SMILES: [N-]=[N+]=NCCCCCNC(=O)COc1cc(/C=C/c2ccccc2)ccc1O] |
| 145 | 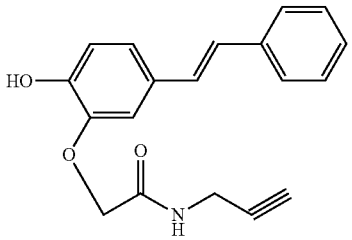 [SMILES: C#CCNC(=O)COc1cc(/C=C/c2ccccc2)ccc1O] |
| 146 | 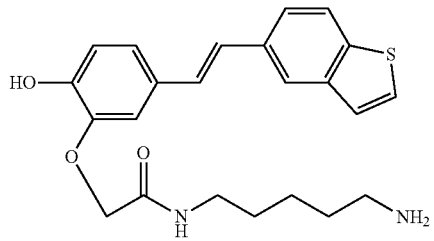 [SMILES: NCCCCCNC(=O)COc1cc(/C=C/c2ccc3sccc3c2)ccc1O] |
| 147 | 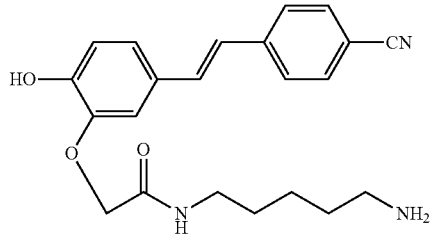 [SMILES: N#Cc1ccc(/C=C/c2ccc(O)c(OCC(=O)NCCCCCN)c2)cc1] |
| 148 | 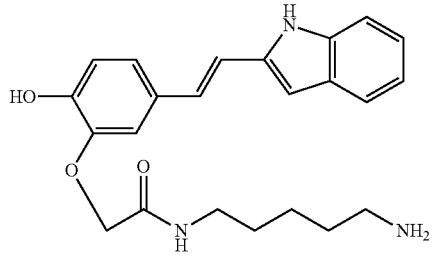 [SMILES: NCCCCCNC(=O)COc1cc(/C=C/c2cc3ccccc3[nH]2)ccc1O] |

TABLE 2-continued
Some styryl phenols useful for making the compounds of invention
| Compound Code | Structure |
|---|---|
| 149 | 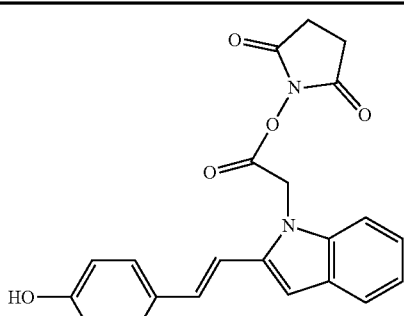 |
| 150 | 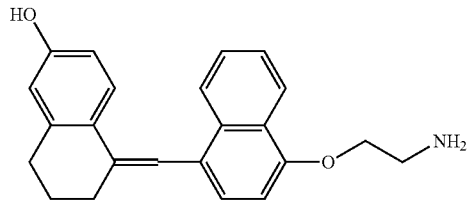 [SMILES: NCCOc1ccc(C=C2CCCc3cc(O)ccc32)c2ccccc12] |
| 151 | 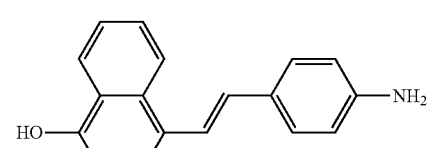 |
| 156 | 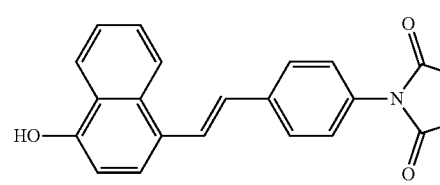 |
| 157 | 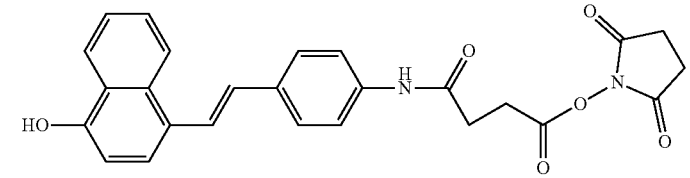 |
| 158 | 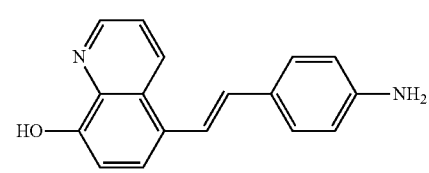 [SMILES: Nc1ccc(/C=C/c2ccc(O)c3ccccc23)cc1] |
| 159 | 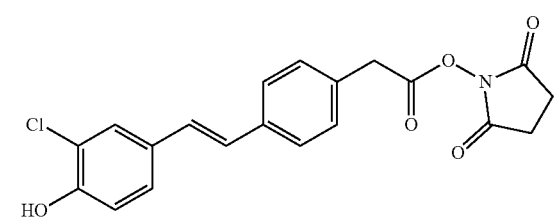 [SMILES: O=C(Cc1ccc(/C=C/c2ccc(O)c(Cl)c2)cc1)ON1C(=O)CCC1=O] |

TABLE 2-continued
Some styryl phenols useful for making the compounds of invention
| Compound Code | Structure |
| --- | --- |
| 160 | 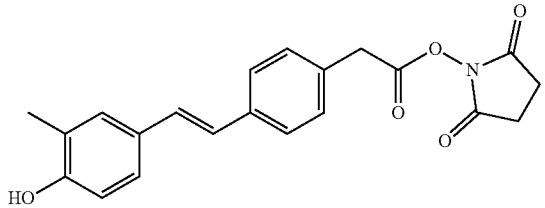 [SMILES: Cc1cc(/C=C/c2ccc(CC(=O)ON3C(=O)CCC3=O)cc2)ccc1O] |
| 161 | 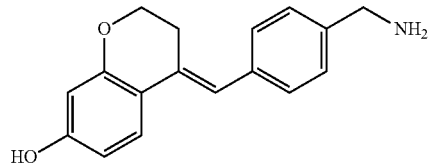 [SMILES: NCc1ccc(/C=C2\CCOc3cc(O)ccc32)cc1] |
| 162 | 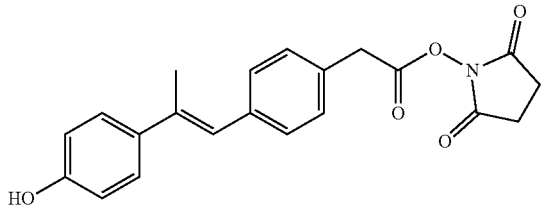 [SMILES: C/C(=C\c1ccc(CC(=O)ON2C(=O)CCC2=O)cc1)c1ccc(O)cc1] |
| 163 | 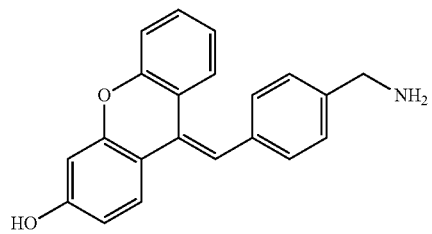 [SMILES: NCc1ccc(/C=C2\c3ccccc3Oc3cc(O)ccc32)cc1] |
| 164 | 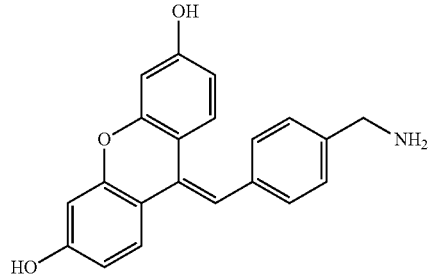 [SMILES: NCc1ccc(C=C2c3ccc(O)cc3Oc3cc(O)ccc32)cc1] |
| 165 | 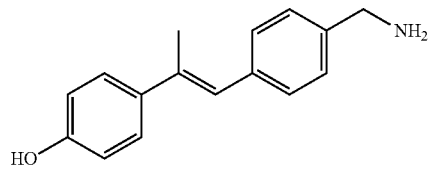 [SMILES: C/C(=C\c1ccc(CN)cc1)c1ccc(O)cc1] |
| 166 | 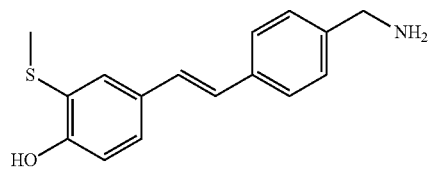 [SMILES: CSc1cc(/C=C/c2ccc(CN)cc2)ccc1O] |

TABLE 2-continued

Some styryl phenols useful for making the compounds of invention

| Compound Code | Structure |
|---|---|
| 167 | 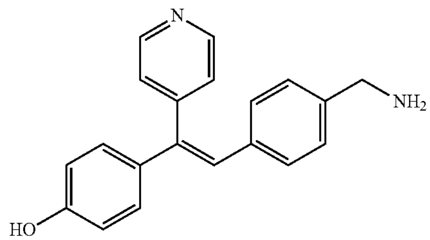 [SMILES: NCc1ccc(/C=C(\c2ccncc2)c2ccc(O)cc2)cc1] |
| 168 | 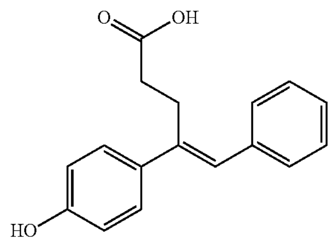 [SMILES: O=C(O)CC/C(=C\c1ccccc1)c1ccc(O)cc1] |
| 169 | 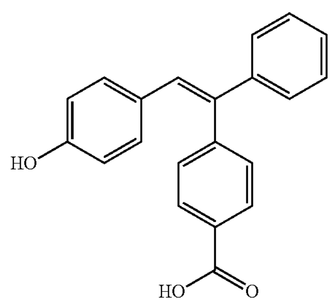 [SMILES: O=C(O)c1ccc(/C(=C\c2ccc(O)cc2)c2ccccc2)cc1] |
| 170 | 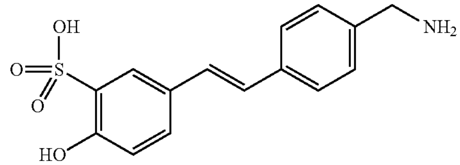 [SMILES: NCc1ccc(/C=C/c2ccc(O)c(S(=O)(=O)O)c2)cc1] |
| 171 | 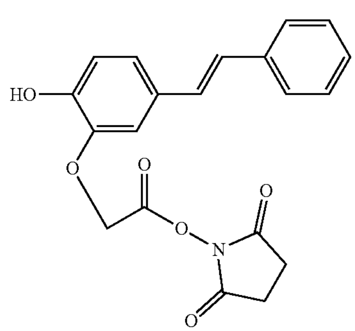 [SMILES: O=C(COc1cc(/C=C/c2ccccc2)ccc1O)ON1C(=O)CCC1=O] |
| 172 | 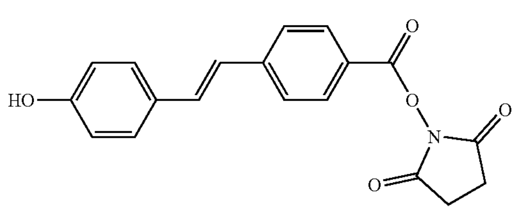 [SMILES: O=C(ON1C(=O)CCC1=O)c1ccc(/C=C/c2ccc(O)cc2)cc1] |

TABLE 2-continued

Some styryl phenols useful for making the compounds of invention

| Compound Code | Structure |
| --- | --- |
| Cy3 | 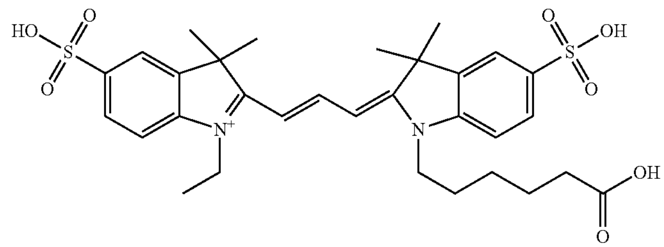 [SMILES: CC[N+]1=C(/C=C/C=C2/N(CCCCCC(=O)O)c3ccc(S(=O)(=O)O)cc3C2(C)C)C(C)(C)c2cc(S(=O)(=O)O)ccc21] |
| Cy3-Tyramide | 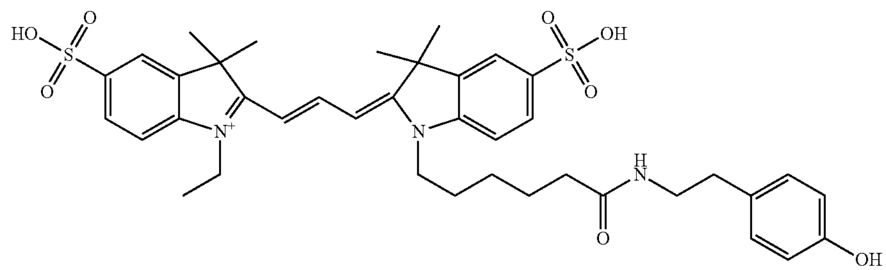 [SMILES: CC[N+]1=C(/C=C/C=C2/N(CCCCCC(=O)NCCc3ccc(O)cc3)c3ccc(S(=O)(=O)O)cc3C2(C)C)C(C)(C)c2cc(S(=O)(=O)O)ccc21] |
| AF488-Tyramide | 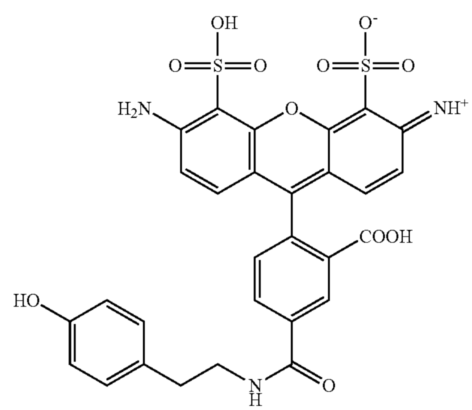 [SMILES: Nc1ccc2c(-c3ccc(C(=O)NCCc4ccc(O)cc4)cc3C(=O)O)c3ccc(=[NH2+])c(S(=O)(=O)[O-])c-3oc2c1S(=O)(=O)O] |
| DAB | 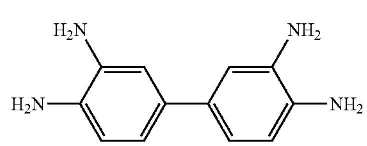 [SMILES: Nc1ccc(-c2ccc(N)c(N)c2)cc1N] |

Example 14. Preparation of Compound 200

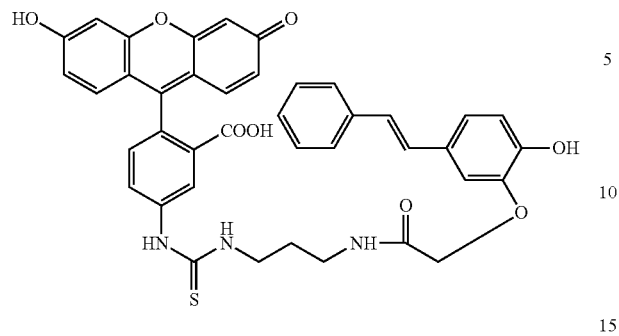

To the DMF solution (1 mL) of 5-FITC cadaverine (20 mg, AAT Bioquest) with 0.5 mL Et$_3$N, Compound 171 is added, and the resulting reaction mixture is allowed to stir at room temperature for 2 hours. After the evaporation of the solvent, the crude is purified by on a silica gel column to give the pure Compound 200 using a gradient of EtOAc/MeOH.

Example 15. Preparation of Compound 201

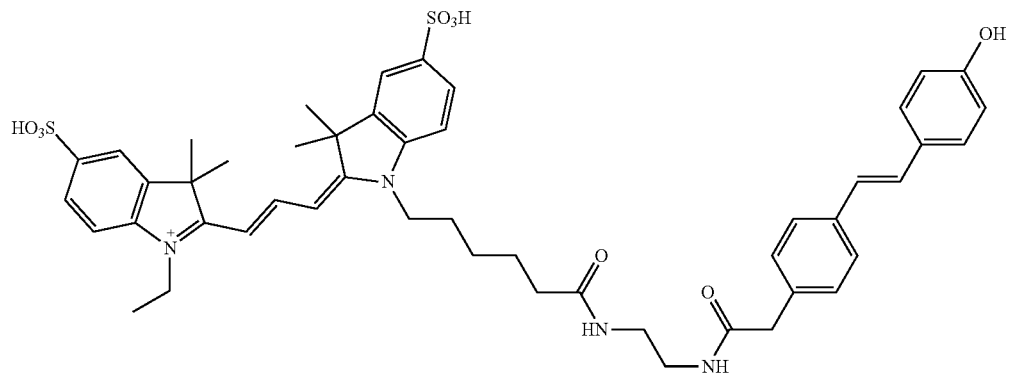

To the DMF solution (2 mL) of Compound 106 (8 mg) with 0.025 mL Et$_3$N, Cy3 amine (AAT Bioquest) is added, and the resulting reaction mixture is allowed to stir at room temperature for 30 minutes. After the evaporation of the solvent, the crude is purified by C-18 column chromatography to give Compound 201 as red solid.

Example 16. Preparation of Compound 202

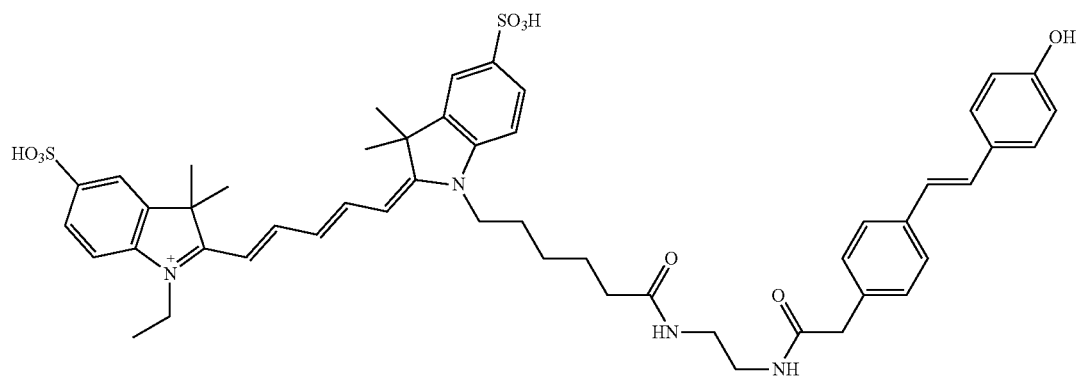

To the DMF solution (2 mL) of Compound 106 (8 mg) with 0.025 mL Et$_3$N, Cy5 amine (AAT Bioquest) is added, and the resulting reaction mixture is allowed to stir at room temperature for 30 minutes. After the evaporation of the solvent, the crude is purified by C-18 column chromatography to give Compound 202 as red solid.

Example 17. Preparation of Compound 203

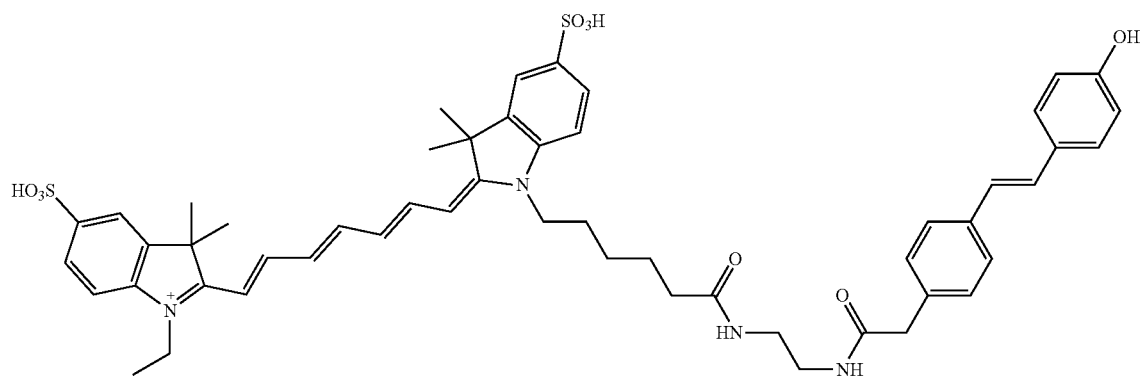

To the DMF solution (2 mL) of Compound 106 (8 mg) with 0.025 mL Et$_3$N, Cy7 amine (AAT Bioquest) is added, and the resulting reaction mixture is allowed to stir at room temperature for 30 minutes. After the evaporation of the solvent, the crude is purified by C-18 column chromatography to give Compound 203 as red solid.

Example 18. Preparation of Compound 204

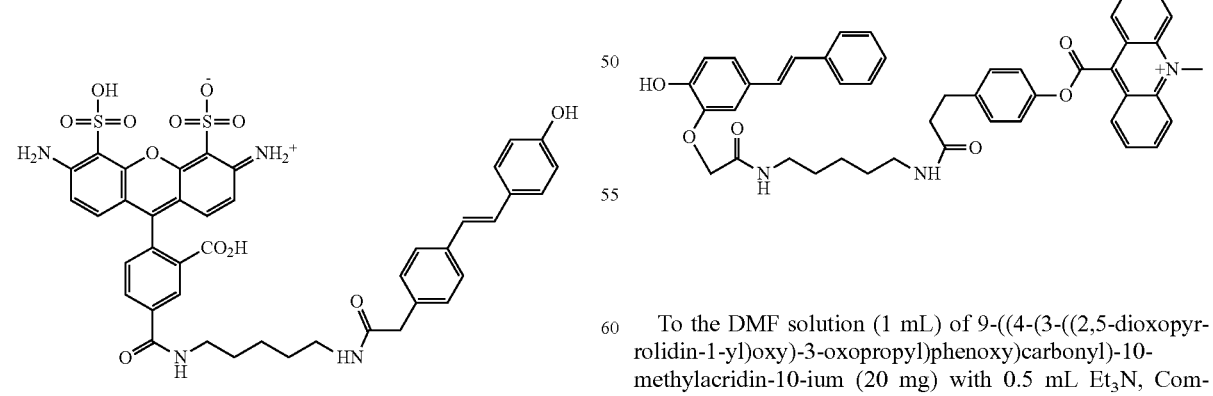

To the DMF solution (2 mL) of Compound 106 (10 mg) with 0.025 mL Et$_3$N, Alexa Fluor 488 amine (10 mg, AAT Bioquest) is added, and the resulting reaction mixture is allowed to stir at room temperature for 2 hours. After the evaporation of the solvent, the crude is purified by C-18 column chromatography to give Compound 204 as red solid.

Example 19. Preparation of Compound 205

To the DMF solution (1 mL) of 9-((4-(3-((2,5-dioxopyrrolidin-1-yl)oxy)-3-oxopropyl)phenoxy)carbonyl)-10-methylacridin-10-ium (20 mg) with 0.5 mL Et$_3$N, Compound 130 is added, and the resulting reaction mixture is allowed to stir at room temperature for 30 minutes. After the evaporation of the solvent, the crude is purified by on a silica gel column to give the pure Compound 205 using a gradient of EtOAc/MeOH.

Example 20. Preparation of Compound 206

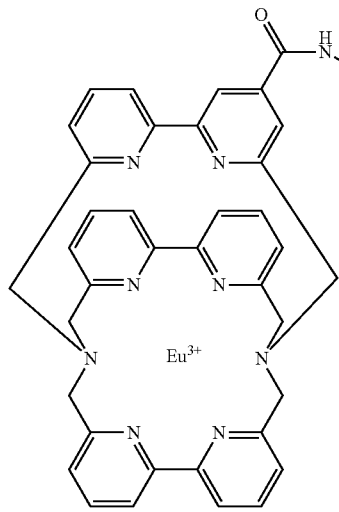
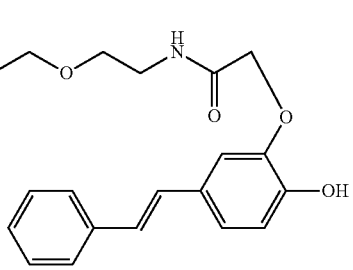

To the DMF solution (1 mL) of cryptate amine (20 mg, Xian Biolite) with 0.5 mL Et$_3$N, Compound 171 is added, and the resulting reaction mixture is allowed to stir at room temperature for 2 hours. After DMF is evaporated, the crude residue is dissolved in 10% EuCl$_3$ methanol solution (5 mL). The MeOH solution is refluxed for 2 hours and cooled to room temperature. The reaction mixture is concentrated, and the residue is washed with EtOAc for multiple times.

Example 21. Preparation of Compound 205
[Poly-Lys-Lys(Cy5)-Lys(Compound 121)]

To the DMF solution (2 mL) of Cy5-labled poly-lysine (MW=3000, AAT Bioquest) and 1 mL Et$_3$N, Compound 121 (10 mg) is added once at room temperature. The resulting reaction mixture is allowed to stir at room temperature for 2 hours. After the evaporation of the solvent, the crude material is dialyzed to remove unreacted Compound 121 and its hydrolyzed acid. The solution is freeze-dried to give poly-lysine labeled with both Compound 121 and Cy5.

Example 22. Preparation of Compound 207
[Polyfluorene-Compound 121 Conjugate]

To the DMF solution (2 mL) of PFO amine (U.S. Pat. No. 9,896,538) and 1 mL Et$_3$N, Compound 121 (10 mg) is added once at room temperature. The resulting reaction mixture is allowed to stir at room temperature for 2 hours. The DMF solution is concentrated under high vacuum and diluted with 10 ml water. The crude material is dialyzed to remove unreacted Compound 121 and its hydrolyzed acid. The solution is concentrated and kept in a freezer.

Example 23. Preparation of Compound 208
[Cy3.5-Polyfluorene-Compound 121 Conjugate]

To the DMF solution (2 mL) of Cy3.5 labeled PFO amine (U.S. Pat. No. 9,896,538) and 1 mL Et$_3$N, Compound 121 (10 mg) is added once at room temperature. The resulting reaction mixture is allowed to stir at room temperature for 2 hours. The DMF solution is concentrated under high vacuum and diluted with 10 ml water. The crude material is dialyzed to remove unreacted Compound 121 and its hydrolyzed acid. The solution is concentrated and kept in a freezer.

Example 24. Preparation of Compound 209
[R-Phycoerythrin-Compound 121 Conjugate]

To the 1 M NaHCO$_3$ solution of R-Phycoerythrin (500 µL, 10 mg/mL) add 10 µL DMSO stock solution of Compound 121 (10 mg/mL). The reaction mixture is rotated at room temperature for 2 hours. The crude material is dialyzed to remove unreacted Compound 121 and its hydrolyzed acid. The solution is concentrated and kept in a refrigerator.

The synthesis of TAG molecules is also well known in the literature (e.g., see H. Zollinger, Color Chemistry, 1991; D. R. Waring et al., The chemistry and Applications of Dyes, 1990; K. Venkataraman, The Chemistry of Synthetic Dyes, 1978; U.S. Pat. Nos. 4,745,181; 4,918,192; 4,946,958; 5,110,932; 5,565,570; 5,656,426; 5,783,699; 8,778,624; 9,575,062). There are now a large number of commercial vendors that offer ready to use reactive dyes that can be conveniently converted to the compounds of the inventions. These vendors include AAT Bioquest, Sigma-Aldrich, ThermoFisher, BD Bioscience, GE Life Science, Broad Pharm, Abcam, Click Chemistry Tools, Lumiprobe, Gold Biosciences, Biotium and Tocris etc.

Example 24. Flow Cytometric Detection of Cytokines with Compounds 200-204

Human peripheral blood mononuclear cells are cultured in RPMI medium containing 10% fetal bovine serum, 10 ng/ml phorbol myristic acetate and 500 ng/ml ionomycin, at 37° C. for 6 hours to induce expression of Interleukin 2. The cells are then harvested and fixed in 100 µL of 1% paraformaldehyde in phosphate buffered saline (PBS) at room temperature for 10 minutes, then permeabilized for 10 minutes at room temperature in 100 µL of 0.2% saponin, 3% hydrogen peroxide, and 1 mg/mL milk proteins in PBS. The cells are then washed in a PBS diluent consisting of PBS with 1% bovine serum albumin and 1% fetal bovine serum. The cells are then treated for 10 minutes at room temperature with 500 ng mouse IgG1 or 500 ng mouse IgG1 anti-human interleukin 2 primary antibody. After being washed, the cells used for standard amplification are incubated with a 1:50 dilution of FITC conjugated F(ab')2 anti-murine Ig (a total of 1.5 µg) in a volume of 50 µL of diluent: 0.2% saponin, 1% bovine serum albumin, and 1% fetal bovine serum in PBS. These cells are washed and then analyzed for fluorescence intensity on a flow cytometer. The cells treated for enzymatic amplification staining are washed after the primary antibody incubation and then incubated with a 1:150 dilution of horseradish peroxidase conjugated F(ab')2 anti-murine Ig in 99.8% fetal bovine serum, 0.2% saponin. After being washed, these cells are incubated at room temperature for 10 minutes with 100 µg/mL Compounds 200-204. The medium for this incubation is 20 mM glycylglycine, pH 8.0 with 1 M NaCl and 0.01% hydrogen peroxide. After this incubation the cells are washed and then analyzed for fluorescence intensity on a flow cytometer. Some cytokines, e.g., Interleukin 2, do not accumulate in cells, but instead are rapidly secreted. Thus, the intracellular levels of such cytokines are typically too low for detection by the standard FITC-labeled antibody. Typically, detection of these intracellular cytokines by flow cytometry relies on the use of one or more metabolic inhibitors that prevent secretion, resulting in an accumulation of the cytokine. In contrast, the method using Compound 200 in combination with horseradish peroxidase conjugated F(ab')2 anti-murine Ig permits the detection of cytokines, such as Interleukin 2, without the need to resort to using metabolic inhibitors.

Example 25. Immunofluorescence Detection of Cells with Compound 200

Jurkat cells are fixed with 4% paraformaldehyde in PBS for 30 min on ice. Pelleted cells are washed with PBS three times and blocked with 1% BSA in PBS for 30 min at room temperature. These non-permeabilized cells are then incubated with mouse CD45 monoclonal antibody (1/1000) in PBST with 1% BSA for 1 h at room temperature. After washing with PBST, cells are incubated with Goat anti-Mouse IgG secondary antibody directly conjugated with Cy3 or HRP-labeled Goat anti-Mouse IgG secondary antibody in PBST with 1% BSA for 1 h at room temperature. Both secondary antibodies are used at the same concentration of 0.8 µg/mL. After incubation with secondary antibodies, all samples are washed with PBST three times. Cells stained with standard method using directly conjugate GAM IgG-Cy3 are resuspended in PBS before analysis. Cells stained with HRP-labeled GAM IgG are further incubated with Cy3-tyramide or Compound 201 in amplification buffer with 0.003% $H_2O_2$. After 10 min amplification reaction at room temperature, cells are washed with PBS three times before data acquisition. Fluorescence images are taken using the TRITC filter set (Ex/Em=545/600 nm) and analyzed with the same exposure time.

Example 26. Flow Cytometric Detection of Protein Kinases with Compound 204

Jurkat cells are fixed, permeabilized and quenched with 3% $H_2O_2$ in MeOH for 30 min at −20° C. Pelleted cells are washed with PBS three times and blocked with 1% BSA in PBS for 30 min at room temperature. Cells are then incubated with rabbit Akt1 phospho (pS473) (1/5000) in PBST with 1% BSA for 1 h at room temperature. After washing with PBST, cells are incubated with Goat anti-Rabbit IgG secondary antibody directly conjugated with Alexa Fluor 488 at 5 µg/mL or HRP-labeled Goat anti-Rabbit IgG secondary antibody at 1 µg/mL in PBST with 1% BSA for 1 h at room temperature. After incubation with secondary antibodies, all samples are washed with PBST three times. Cells stained using directly conjugate GAR IgG-AF488 are resuspended in PBS before analysis. Cells stained with HRP-labeled GAR IgG are further incubated with AF488-tyramide (ThermoFisher Scientific) or Compound 204 in amplification buffer with 0.003% $H_2O_2$. After 10 min amplification reaction at room temperature, cells are washed with PBS three times before data acquisition. Fluorescence intensity is measured using ACEA NovoCyte flow cytometer in FITC channel (Ex/Em=488/530 nm).

Example 27. Fluorescence Imaging of Cancer Tissues with Compounds 200-204

Formalin fixed, paraffin embedded (FFPE) tissue sections from cancer patient with lung adenocarcinoma are deparaffinized and rehydrated in serial solutions of xylene, ethanol and water. The dewaxed sections are antigen retrieved for 20 min in citrate buffer, and the endogenous peroxidase activity is inhibited by incubating sections in 3% $H_2O_2$ in PBS for 10 min. Slides are then washed in PBS and incubated in PBS blocking buffer containing 1% BSA and 10% goat serum for 30 min. The sections are incubated with monoclonal rabbit antibody directed against human EpCAM (1/200) in PBS blocking buffer overnight at 4° C. After multiple washings in PBST, slides are incubated for 1 hour at room temperature with Goat anti-Rabbit IgG secondary antibody directly conjugated with Cy3 or polyHRP-conjugated Goat anti-Rabbit IgG secondary antibody. Tissues stained with polyHRP-GAR IgG are further incubated with Cy3-tyramide or Compound 201 in amplification buffer with 0.003% $H_2O_2$. After 10 min amplification reaction at room temperature, tissues are washed with PBST three times followed by preservation in antifading mounting medium. Fluorescence images are taken using the TRITC filter set (Ex/Em=545/600 nm) and analyzed with the same exposure time.

Example 28. Fluorescence Imaging of Her 2-Positive Tissues

Human Her2/Neu (c-erbB-2) positive tissue sections are deparaffinized and rehydrated in serial solutions of xylene, ethanol and water. The dewaxed sections are antigen retrieved for 20 min in citrate buffer, and the endogenous peroxidase activity is inhibited by incubating sections in 3% $H_2O_2$ in PBS for 10 min. Slides are then washed in PBS and incubated in PBS blocking buffer containing 1% BSA and 10% goat serum for 30 min. The sections are incubated with monoclonal rabbit antibody directed against human HER2/ErbB2 (1/2000) in PBS blocking buffer overnight at 4° C. After multiple washing in PBST, slides are incubated for 1 hour at room temperature with Goat anti-Rabbit IgG secondary antibody directly conjugated with Cy3 or polyHRP-conjugated Goat anti-Rabbit IgG secondary antibody. Tissues stained with polyHRP-GAR IgG are further incubated with Cy3-TSA or Compound 201 in amplification buffer with 0.003% $H_2O_2$. After 10 min amplification reaction at room temperature, tissues are washed with PBST three times followed by preservation in antifading mounting medium. Fluorescence images are taken using the TRITC filter set (Ex/Em=545/600 nm) and analyzed with the same exposure time.

Example 29. Color Imaging of Cancer Tissues

Formalin fixed, paraffin embedded (FFPE) tissue sections from cancer patient with lung adenocarcinoma are dewaxed, antigen retrieved, quenched and blocked as before. The sections are then incubated with monoclonal rabbit antibody directed against human EpCAM (1/200) in PBS blocking buffer overnight at 4° C. After multiple washing in PBST, slides are incubated for 1 hour at room temperature with polyHRP-conjugated Goat anti-Rabbit IgG secondary antibody. Tissues are further incubated with either DAB or Compound 201 in amplification buffer for 10 min. After counterstain in hematoxylin and dehydration in serial solutions of water, ethanol and xylene, the tissues are preserved in organic mounting medium. The bright field images are captured with the same exposure time.

What is claimed is:

1. A method of detecting a target in a sample, wherein the method comprises the steps of:
   (i) incubating a target with one or more binding agents comprising a peroxidase conjugate, wherein the one or more binding agents is/are capable of direct or indirect binding to the target, forming a complex comprising the target and one or more binding agents, wherein at least one binding agent comprises peroxidase activity;
   (ii) incubating the complex of (i) with a peroxide compound and a compound of Formula 1

Formula 1

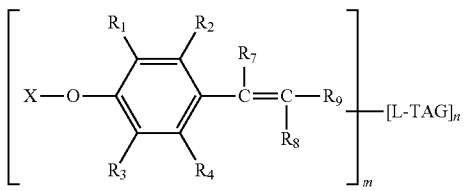

wherein,
$R_1$-$R_4$ are each H;
$R_7$ and $R_8$ are each H;
$R_9$ is phenyl;
X is hydrogen, or a counter cation;
L is a linker;
TAG is a biologically detectable moiety connected to $R_9$ via the linker L; and m and n are independently an integer from 1 to 100,
wherein the compound is capable of functioning as a detectable substrate for a peroxidase enzyme or a peroxidase conjugate to provide a deposited compound; and
(iii) detecting the deposited compound, and thereby detecting the target.

2. The method of claim 1, wherein the compound is of Formula 3

Formula 3

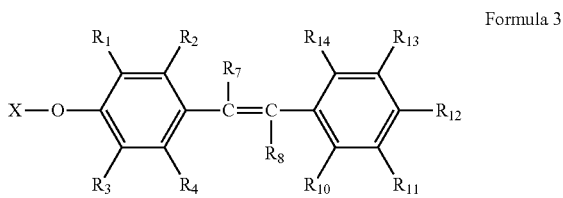

wherein,
$R_1$-$R_4$ are each H, and $R_{10}$-$R_{14}$ are independently H, or [L-TAG]n wherein at least one of the $R_{10}$-$R_{14}$ is [L-TAG]n;
$R_7$ and $R_8$ are each H;
X is hydrogen, or a counter cation;
L is a linker;
TAG is a dye, a biotin, FITC, DNP, DIG, a luminol, an acridinium ester, a ruthenium complex, an europium complex, a terbium complex, a fluorescent protein, a fluorescent conjugated polymer, or a quantum dot; and
n is an integer from 1 to 100.

3. The method of claim 2, wherein $R_{12}$ is [L-TAG]n.
4. The method of claim 1, wherein X is hydrogen.
5. The method of claim 1, wherein TAG is a dye.
6. The method of claim 1, wherein n is 1.
7. The method of claim 3, wherein X is hydrogen, TAG is a dye and n is 1.
8. The method of claim 7, wherein the compound is selected from a group of compounds consisting of:

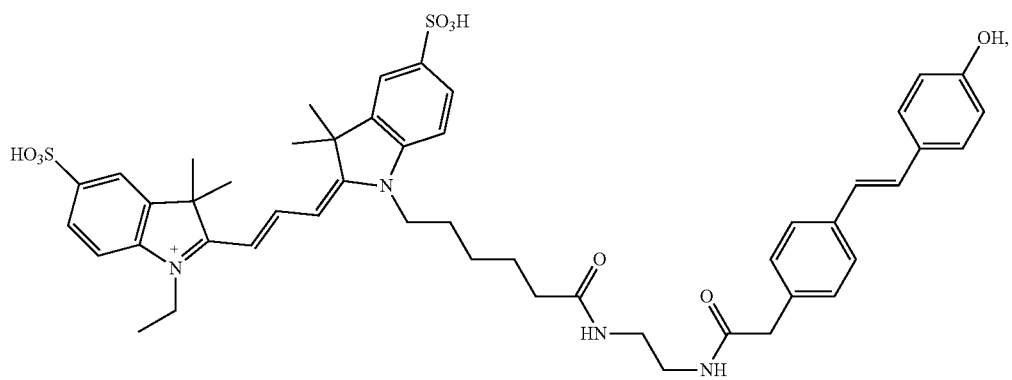

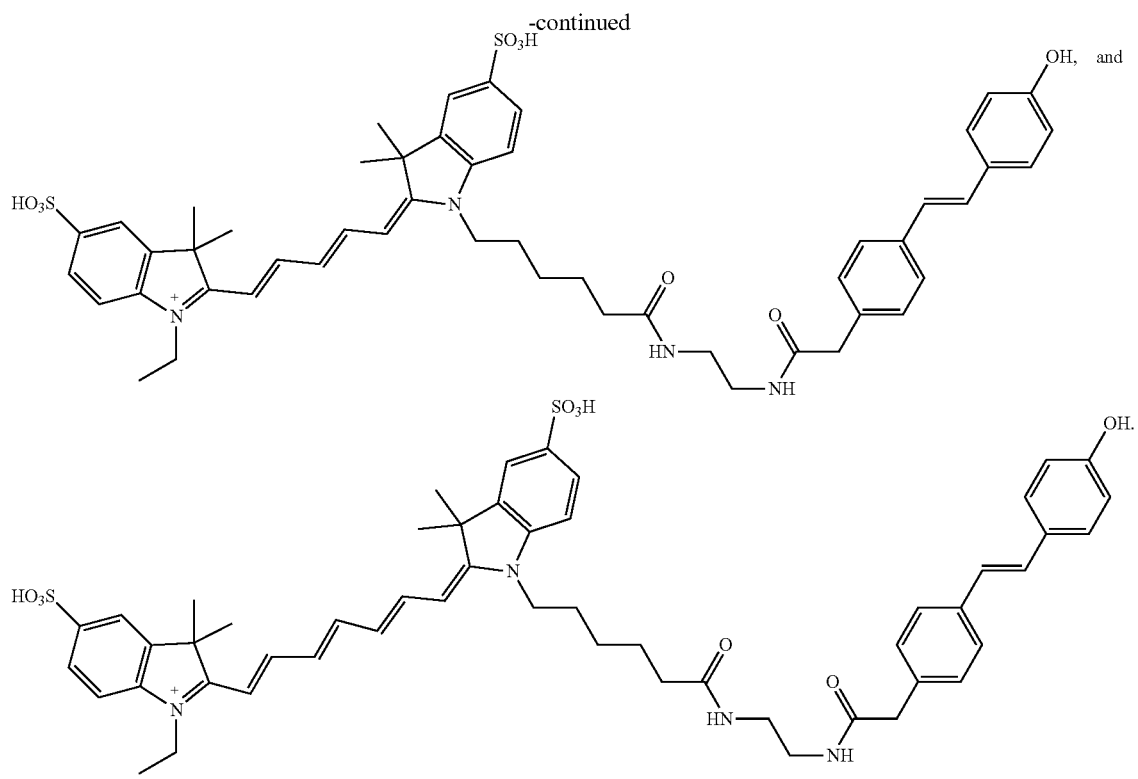

9. A method of detecting a target in a sample, wherein the method comprises the steps of:
(i) incubating a target with one or more binding agents comprising a peroxidase conjugate, wherein the one or more binding agents is/are capable of direct or indirect binding to the target, forming a complex comprising the target and one or more binding agents, wherein at least one binding agent comprises peroxidase activity;
(ii) incubating the complex of (i) with a peroxide compound of the following Formula

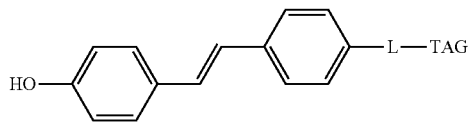

wherein,
L is a linker; and
TAG is a biologically detectable moiety;
wherein the compound is capable of functioning as a detectable substrate for a peroxidase enzyme or a peroxidase conjugate to provide a deposited compound; and
(iii) detecting the deposited compound, and thereby detecting the target.

10. The method of claim 9, wherein TAG is a dye, a biotin, FITC, DNP, DIG, a luminol, an acridinium ester, a ruthenium complex, an europium complex, a terbium complex, a fluorescent protein, a fluorescent conjugated polymer, a quantum dot, or a radioactive isotope.

11. The method of claim 10, wherein TAG is a dye.

12. The method of claim 11, wherein the dye is selected from the group consisting of acridines, acridiniums, acridones, anthraquinones, azo dyes, azin dyes, phthalocyanines, Eurhodin dyes, safranins, indamins, indophenols, oxazines, thiazines, oxazoles, thiazoles, polythiophenes, polypyrroles, pyronins, pyryliums, fluoresceins, rhodamines, coumarins, cyanines, porphyrins, rhodols, quinolines, bodipy dyes, squaraines, perylenediimides, diketopyrrolopyrroles, conjugated polymers, fluorescent proteins, quantum dots, and polymer dots.

13. The method of claim 12, wherein dye is a cyanine dye.

14. The method of claim 9, wherein the linker L comprises 1-20 non-hydrogen atoms.

15. The method of claim 14, wherein the linker L is composed of any combination of bonds selected from single carbon-carbon bonds, carboxamide bonds and thioether bonds.

16. The method of claim 14, wherein the linker L is of the following formula:

wherein:
a is 0 to 10;
b is 1 to 10; and
z is 1 to 5.

* * * * *